US012658444B2

(12) United States Patent
Ye et al.

(10) Patent No.: US 12,658,444 B2
(45) Date of Patent: Jun. 16, 2026

(54) NITRO-SUBSTITUTED AROMATIC COMPOUNDS FOR USE IN ELECTRODES

(71) Applicant: VALORBEC, S.E.C., Quebec (CA)

(72) Inventors: Zhibin Ye, Beaconsfield (CA); Xudong Liu, Montreal (CA)

(73) Assignees: Zhibin Ye, Beaconsfield (CA); Xudong Liu, Montreal (CA)

( * ) Notice: Subject to any disclaimer, the term of this patent is extended or adjusted under 35 U.S.C. 154(b) by 1019 days.

(21) Appl. No.: 17/757,192

(22) PCT Filed: Dec. 2, 2020

(86) PCT No.: PCT/CA2020/051646
§ 371 (c)(1),
(2) Date: Jun. 10, 2022

(87) PCT Pub. No.: WO2021/108901
PCT Pub. Date: Jun. 10, 2021

(65) Prior Publication Data

US 2024/0014395 A1 Jan. 11, 2024

Related U.S. Application Data

(60) Provisional application No. 62/944,733, filed on Dec. 6, 2019.

(51) Int. Cl.

| | |
|---|---|
| ***H01M 4/60*** | (2006.01) |
| ***C07C 205/06*** | (2006.01) |
| ***C07C 205/11*** | (2006.01) |
| ***C07C 205/57*** | (2006.01) |
| ***C08F 8/30*** | (2006.01) |
| ***C08F 12/26*** | (2006.01) |

(52) U.S. Cl.
CPC ........... *H01M 4/604* (2013.01); *C07C 205/06* (2013.01); *C07C 205/11* (2013.01); *C07C 205/57* (2013.01); *C08F 8/30* (2013.01); *C08F 12/26* (2013.01); *C07C 2603/18* (2017.05)

(58) Field of Classification Search
CPC . C07C 205/06; C07C 205/12; C07C 2603/18; C07C 205/57; C07C 205/11; H01M 4/668; H01M 4/669; H01M 4/808; H01M 10/0525; H01M 4/622; H01M 4/623; H01M 4/661; H01M 4/667; H01M 4/13; H01M 4/664; H01M 4/60; H01M 4/587; H01M 4/137; H01M 4/625; H01M 4/663; H01M 2300/0025; H01M 4/133; H01M 4/604; H01G 11/38; H01G 11/36; H01G 11/48; C08F 12/26; C08F 8/30; Y02E 60/10
See application file for complete search history.

(56) References Cited

U.S. PATENT DOCUMENTS

2008/0253022 A1 10/2008 Biskeborn et al.
2013/0059193 A1 * 3/2013 Scordilis-Kelley .......................... H01M 10/4235 429/188

FOREIGN PATENT DOCUMENTS

| | | | |
|---|---|---|---|
| CN | 103456961 | A | 12/2013 |
| CN | 1052066838 | A | 12/2015 |
| CN | 106046716 | A | 10/2016 |
| CN | 106602019 | * | 4/2017 |
| CN | 106602019 | A | 4/2017 |
| CN | 106654200 | A | 5/2017 |
| CN | 106654273 | A | 5/2017 |
| CN | 106910895 | A | 6/2017 |
| CN | 106328949 | A | 11/2017 |
| CN | 108598481 | A | 9/2018 |
| CN | 108711624 | A | 10/2018 |
| CN | 108767257 | A | 11/2018 |
| CN | 109802122 | A | 5/2019 |
| CN | 110183655 | B | 8/2019 |
| CN | 110224140 | A | 9/2019 |
| JP | 2003142100 | A | 5/2003 |
| JP | 2010-024127 | * | 2/2010 |
| WO | 2019068182 | A1 | 4/2019 |

OTHER PUBLICATIONS

Luo, Ad. Mater. 2018, 30, 1706498, p. 1-9. (Year: 2018).*
Translation of JP 2010-024127 (Year: 2010).*
Translation of CN 106602019 (Year: 2017).*
Alberny et al., A novel electrode for electrochemical ESR and its application to modified electrodes, Journal of the American Chemical Society, 1984, vol. 106, No. 3, pp. 469-473.
Chen et al., A macrocylic receptor containing two viologen species connected to conjugated terphenyl groups, Org. Biomol. Chem., 2018, vol. 16, pp. 5006-5015.
D'Amato et al., Pressure-induced Cis to Trans Isomerization of Poly-((p-nitrophenyl)acetylene) prepared using Rh Complex catalyst. Extension of π conjugation length.
Iftimie et al., Enhancing the performance of microbial fuel celles (MFCs) with nitrophenyl modified carbon nanotubes-based anode, Applied Surface Science, 2019, vol. 492, pp. 661-668.
Luo et al., Azo Compounds Derived from Electrochemical Reduction of Nitro Compounds for High Performance Li-Ion Batteries, Adv. Mater. 2018, 1706498.
Mauger et al., Recent Progress on Organic Electrodes Materials for Rechargeable Batteries and Supercapacitors, Materials, 2019, vol. 12, pp. 1770.

(Continued)

*Primary Examiner* — Robert C Boyle

(57) ABSTRACT

There is provided the use of a nitro-substituted aromatic compound of formula (I), (II), (III), or (IV) and a copolymers comprising repeat units of formula (III) and/or (IV) as an electrode material as well as the use of such compound in the manufacture of an electrode. An electrode composite material and an electrode comprising this compound are also provided. When used in metal-ion batteries, preferably Li-ion batteries, the electrode of the invention has a combination of high operating voltage (e.g. >2.0 V) and high specific capacities (e.g. >300 mAh $g^{-1}$). To the best of the inventors' knowledge, some of them have the highest specific capacity, along N with high voltage, among organic electrode materials reported to date for application in alkali-ion batteries. (I), (II), (III), (IV).

2 Claims, 27 Drawing Sheets

(56) References Cited

OTHER PUBLICATIONS

Murray et al., Oxidation of primary amides dimethyldioxirane, J. Org. Chem. 1989, 54, pp. 5783-5788.
Philippides et al., The nitration of polystyrene, Polymer, 1993, vol. 34, 16, pp. 3509-3513.
Renuka, 2-β-Dinitrostyrene as as cathode material in a magnesium/zinc-based primary battery, Journal of Power Sources, 2000, vol. 87, pp. 4-11.
Satheesh et al., Synthesis and characterization of nitro-functionalized electrochemically exfoliated graphene, Materials Letters, 2014, vol. 137, pp. 153-155.
Sivasamy et al., Mono-chloro-subsituted m-dinitrobenzene compounds as cathode materials in magnesium battery, B. Electrochem, Apr. 1968, vol. 4(4), pp. 347-350.
Starkey, p-Dinitrobenzene, Organic Syntheses, 1939, vol. 19, pp. 40.

* cited by examiner

NITRO-SUBSTITUTED AROMATIC COMPOUNDS FOR USE IN ELECTRODES

CROSS REFERENCE TO RELATED APPLICATIONS

This application claims benefit, under 35 U.S.C. § 119(e), of U.S. provisional application Ser. No. 62/944,733, filed on Dec. 6, 2019. All documents above are incorporated herein in their entirety by reference.

FIELD OF THE INVENTION

The present invention relates to nitro-substituted aromatic compounds. More specifically, the present invention is concerned with the use of such compounds as an electrode material as well as the use of such compounds in the manufacture of an electrode.

BACKGROUND OF THE INVENTION

To meet the ever-increasing need in powering electronic devices and vehicles, it is extremely desirable to develop new and sustainable battery technologies possessing higher and cleaner electrical-storage capabilities. Currently, rechargeable lithium ion batteries (LIBs) have the dominant market of portable electronics owing to their high energy density, long cycle life, and other excellent performance characteristics. Due to the limited natural abundance of lithium, batteries based on other metals (such as sodium, potassium, magnesium, aluminum, etc.) of higher natural abundance and lower costs are also being developed. However, current rechargeable batteries have been built predominantly with inorganic material-based electrodes (e.g., transition metal oxides), particularly those materials with conventional insertion mechanisms. In terms of theoretical storage capacity (generally, <300 mAh $g^{-1}$) and energy density, there is limited room for further improvements with inorganic materials. Meanwhile, these inorganic materials have limited earth abundance and present serious environmental issues.

In this regard, organic electrode materials have received significant attention owing to their distinct advantages, including construction from naturally abundant elements (C, H, N, O, S) of low atomic weights, multi-redox ability, tunable structures, and environmental friendliness. For organic electrode materials, energy storage is achieved through the redox reaction of the metal ions and the organic functional groups. Various synthetic strategies have been adopted to obtain organic electrode materials with appropriate functional groups and adjusted structures for enhanced metal ion storage performance. Up to now, different types of organic materials, such as molecules containing free radicals, conductive polymers, conjugated carbonyl-containing compounds, have been explored as the electrode materials for metal ion batteries. However, most organic electrode materials discovered thus far usually exhibit small reversible capacities (<400 mAh $g^{-1}$). More importantly, organic electrode materials with higher operating voltages (>2.0 V) have even lowered effective capacities (<300 mAh $g^{-1}$), which severely restricts their applications in large-scale energy storage devices. As such, it is still challenging to find satisfactory organic electrode materials.

SUMMARY OF THE INVENTION

In accordance with the present invention, there is provided:

1. Use of a nitro-substituted aromatic compound as an electrode material, wherein the nitro-substituted aromatic compound is of formula (I), (II), (III), or (IV):

(I)

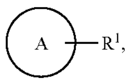

(II)

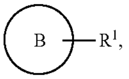

(III)

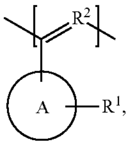

or (IV)

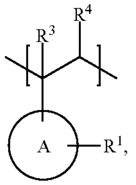

or a copolymer comprising repeat units of formula (III) and/or (IV), wherein:

A represents an arene or heteroarene,

B represents an aromatic carbon allotrope, which is optionally doped with one or more heteroatoms, $R^1$ represents one or more -L-$NO_2$ substituents, $R^2$ represents =N—, =CH—, or =$CR^5$—, and $R^3$ and $R^4$ independently represents a hydrogen atom or $R^5$, wherein A and B are optionally further substituted by one or more $R^5$, wherein L represents a covalent bond or a linking group, and wherein each —$R^5$ independently represents $R^6$, —X, —$NH_2$, —$NR^6H$, —$NR^{62}$, —CN, —CHO, —COOH, —$COOR^6$, —COO— $M^+$, —OH, —$OR^6$, or —$O^-$ $M^+$ group, in which:

$R^6$ represents an alkyl, alkenyl, alkynyl, alkenylyl, or aryl, or heteroaryl group, M represents a metal ion, and X represents a halogen atom.

2. Use of a nitro-substituted aromatic compound in the manufacture of an electrode, wherein the nitro-substituted aromatic compound is of formula (I), (II), (III), or (IV) as defined in item 1.
3. An electrode composite material comprising a nitro-substituted aromatic compound, wherein the nitro-substituted aromatic compound is of formula (I), (II), (III), or (IV) as defined in item 1.
4. An electrode comprising a nitro-substituted aromatic compound, wherein the nitro-substituted aromatic compound is of formula (I), (II), (III), or (IV) as defined in item 1.
5. The use/electrode composite material/electrode of any one of items 1 to 4, wherein the nitro-substituted aromatic compound is of formula (I) or (IV), more preferably of formula (I).

6. The use/electrode composite material/electrode of any one of items 1 to 5, wherein A represents benzene, naphthalene, anthracene, phenanthrene, fluorene, phenalene, tetracene, chrysene, triphenylene, fluoranthene, pyrene, benzo[c]fluorene, pentacene, pentacyclo [13.3.1.0$^{5}$,$^{18}$0.0$^{8}$,$^{17}$ 0.0$^{11}$,$^{16}$]nonadeca-1,3,5(18),7,9,11, 13,15(19),16-nonaene, benzo[a]pyrene, corannulene, benzo[ghi]perylene, coronene, ovalene, or hexa-peri-hexabenzocoronene, biphenyl, terphenyl, triphenylmethane, tetraphenylmethane, tetracyclo[13.3.1. 1$^{3}$,$^{7}$0.1$^{9}$,$^{13}$]henicosa-1(19),3,5,7(21),9,11,13(20),15, 17-nonaene, pentacyclo[20.3.1.1$^{3}$,$^{7}$0.1$^{9}$,$^{13}$0.0$^{15}$,$^{20}$]octacosa-1(26),3,5,7(28),9,11,13(27),15,17,19,22,24-dodecaene, or heptacyclo[25.3.1.1$^{2}$,$^{6}$, 0.1$^{7}$,$^{11}$, 0.1$^{12}$,$^{16}$, 0.1$^{17}$,$^{21}$, 0.1$^{22}$,$^{26}$]hexatriaconta-1(31),2(36),3,5,7,9,11 (35),12(34),13,15,17,19,21(3 3),22(32),23,25,27,29-octadecaene, or corresponding heteroarenes, or furan, thiophene, pyrrole, pyrazole, isoxazole, imidazole, oxazole, isothiazole, thiazole, pyridine, pyrimidine, pyrazine, pyridazine, benzothiophene, quinoline, isoquinoline, purine, pteridine, phenoxazine, phenothiazine, acridine, or phenanthridine;

preferably, A represents an arene, preferably selected among the above;

more preferably, A represents benzene, naphthalene, anthracene, pyrene, or pentacyclo[13.3.1.0$^{5}$,$^{18}$0.0$^{8}$,$^{17}$, 0.0$^{11}$,$^{16}$]nonadeca-1,3,5(18),7,9,11,13,15(19),16-nonaene;

yet more preferably, A represents benzene or naphthalene, and most preferably, A represents benzene.

7. The use/electrode composite material/electrode of any one of items 1 to 6, wherein B represents graphite, graphene, fullerenes, carbon nanotubes, carbon nanobuds, carbon nanorods, carbon nanofibers, carbon nanosphere, or activated carbon, all of which optionally doped with one or more heteroatoms (preferably undoped); and preferably B represents carbon nanotubes, graphene, carbon nanofibers, or carbon nanospheres all of which optionally doped with one or more heteroatoms (preferably undoped).

8. The use/electrode composite material/electrode of any one of items 1 to 7, wherein all -L-$NO_2$ substituents are identical.

9. The use/electrode composite material/electrode of any one of items 1 to 8, wherein the nitro-substituted aromatic compound is of formula (I), (III), or (IV) and -L-$R^1$ represents one to three -L-$NO_2$ substituents; preferably two or three -L-$NO_2$ substituents, and more preferably two -L-$NO_2$ substituents.

10. The use/electrode composite material/electrode of any one of items 1 to 8, wherein the nitro-substituted aromatic compound is of formula (II) and -L-$R^1$ represents a number of -L-$NO_2$ substituents sufficient to functionalize the aromatic carbon allotrope.

11. The use/electrode composite material/electrode of any one of items 1 to 10, wherein the linking group is alkylene, alkenylene, alkynylene, or alkenylylene, each of which being:

optionally substituted with one or more $R^6$, —X, —$NH_2$, —$NR^6H$, —$NR^{62}$, —CN, —CHO, —COOH, —$COOR^6$, —COO-M+, —OH, —$OR^6$, and/or —O— M+, and optionally interrupted with one or more —O—, —$NR^6$—, —NH—, and/or —S—, wherein $R^6$ is as defined above 12. The use/electrode composite material/electrode of any one of items 1 to 11, wherein L represents a covalent bond.

13. The use/electrode composite material/electrode of any one of items 1 to 12, wherein $R^2$ represents ═CH—.

14. The use/electrode composite material/electrode of any one of items 1 to 13, wherein both $R^3$ and $R^4$ represent hydrogen atoms.

15. The use/electrode composite material/electrode of any one of items 1 to 14, wherein A and B are free of $R^5$ substituents.

16. The use/electrode composite material/electrode of any one of items 1 to 14, wherein A and B are substituted by one or more $R^5$ substituents.

17. The use/electrode composite material/electrode of any one of items 1 to 16, wherein $R^5$ represents —$COO^-$ $M^+$, preferably wherein M is an alkaline metal ion, preferably a $Li^+$, $Na^+$, or $K^+$.

18. The use/electrode composite material/electrode of any one of items 1 to 17, wherein the nitro-substituted aromatic compound is of formula (I).

19. The use/electrode composite material/electrode of item 18, wherein the nitro-substituted aromatic compound is a halonitrobenzene, a dinitrobenzene, a dinitrobenzoic acid, a dinitrobenzoic acid salt, a dinitronaphthalene, a dinitronaphthalene, a dinitrobiphenyl, a tris(nitrophenyl)methane, a dinitrofluorene, a poly(nitrostyrene), or nitrated polystyrene;

preferably 1-bromo-4-nitrobenzene, 1,4-dinitrobenzene, 1,3-dinitrobenzene, 1,2-dinitrobenzene, 3,5-dinitrobenzoic acid, 3,5-dinitrobenzoic acid lithium salt, 3,5-dinitrobenzoic acid sodium salt, 3,5-dinitrobenzoic acid potassium salt,1,5-dinitronaphthalene, 1,8-dinitronaphthalene, 4,4'-dinitrobiphenyl, tris(4-nitrophenyl) methane, 2,7-dinitrofluorene, poly(3-nitrostyrene), or nitrated polystyrene; and more preferably 1,4-dinitrobenzene; 3,5-dinitrobenzoic acid lithium salt; or nitrated polystyrene.

20. The use/electrode composite material/electrode of any one of items 1 to 17, wherein the nitro-substituted aromatic compound is of formula (II).

21. The use/electrode composite material/electrode of any one of items 1 to 17, wherein the nitro-substituted aromatic compound is of formula (III) or (IV).

22. The use/electrode composite material/electrode of item 21, wherein the nitro-substituted aromatic compound is nitro-substituted polyphenylacetylene or nitro-substituted polystyrene, preferably nitro-substituted polystyrene.

23. The use/electrode composite material/electrode of any one of items 1 to 17, wherein the nitro-substituted aromatic compound is said copolymer.

24. The use/electrode composite material/electrode of item 23, wherein the repeat units of formula (III) or (IV) in the copolymers are nitro-substituted polyphenylacetylene or nitro-substituted polystyrene, preferably nitro-substituted polystyrene.

25. The use/electrode composite material/electrode of item 23 or 24, wherein other repeat units in the copolymers are repeat units of formula (III') and/or (IV'):

(III')

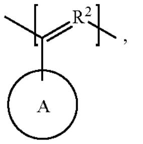

or (IV')

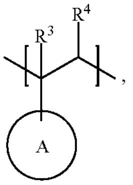

wherein A, $R_2$, $R_3$, and $R_4$ are as defined in the preceding items, other styrenic repeat units, other acetylenic repeat units, acrylates and/or methacrylates.

26. The use/electrode composite material/electrode of any one of items 1 to 25, wherein the nitro-substituted aromatic compound is used in admixture or forming a composite with an aromatic compound.
27. The use/electrode composite material/electrode of item 26, wherein the aromatic compound is of formula (I'), (II'), (III'), or (IV'):

(I')

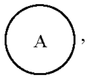

(II')

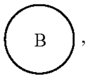

(III')

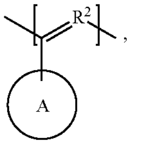

or (IV')

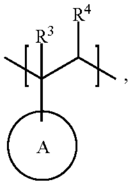

wherein A, B, $R_2$, $R_3$, and $R_4$ are as defined in the preceding items.

28. The use/electrode composite material/electrode of item 27, wherein a composite comprising an aromatic compound of formula (II') dispersed in a matrix of a nitro-substituted aromatic compound of formula (III) and/or (IV).
29. The use/electrode composite material/electrode of any one of items 1 to 28, wherein two or more nitro-substituted aromatic compound are used.
30. The use/electrode composite material/electrode of any one of items 1 to 29, wherein a composite comprising a nitro-substituted aromatic compound of formula (II) dispersed in a matrix of a nitro-substituted aromatic compound of formula (III) or (IV) is used.
31. The use/electrode composite material/electrode of any one of items 1 to 30, wherein the nitro-substituted aromatic compound is used, preferably in a mixture, with a binder and/or a conducting material.
32. The use/electrode composite material/electrode of item 31, wherein the binder is present.
33. The use/electrode composite material/electrode of item 31 or 32, wherein the binder is Nafion® (sulfonated tetrafluoroethylene-based fluoropolymer-copolymer), polytetrafluoroethylene (PTFE) or polyvinylidene fluoride (PVDF); preferably Nafion®.
34. The use/electrode composite material/electrode of any one of items 31 to 33, wherein the conducting material is present.
35. The use/electrode composite material/electrode of any one of items 31 to 34, wherein the conducting material is acetylene black, carbon nanotubes, graphene, of porous activated carbon; preferably acetylene black.
36. The use/electrode composite material/electrode of any one of items 31 to 35, wherein a nitro-substituted aromatic compound:conductive material:binder weight ratio is in the following range about 30-100:0-50:0-15, preferably about 30-95:5-50:5-15, more preferably about 55-90:5-30:5-15, yet more preferably about 73-88:5-15:7-12, and most preferably the weight ratio is about 80:10:10.
37. The use/electrode composite material/electrode of any one of items 1 to 36, wherein the electrode comprises a current collector and the electrode composite material or the mixture disposed on the current collector.
38. The use/electrode composite material/electrode of item 37, wherein the electrode composite material or the mixture forms a film on the current collector.
39. The use/electrode composite material/electrode of item 37 or 38, wherein current collector is:
    a metal foil or grid, which can be carbon-coated,
    a metal foam,
    a graphite plate,
    a carbon foam,
    a polymer film coated with a metal, or
    glass coated with a metal, wherein, in all cases, the metal is preferably gold (Au), platinum (Pt), titanium (Ti), copper (Cu), nickel (Ni), aluminum (Al), or stainless-steel.

40. The use/electrode composite material/electrode of any one or items 37 to 39, wherein the current collector is a metal foil, preferably an Al foil, and more preferably a carbon-coated Al foil.
41. The use/electrode composite material/electrode of item 39 or 40, wherein the metal foil is from about 5 μm to about 50 μm thick.
42. The use/electrode composite material/electrode of any one of items 37 to 41 wherein the current collector may have a finely texture surface to form an effective contact with the composite.
43. A nitro-substituted aromatic compound is of formula (I), (II), (III), or (IV) as defined above in any one of items 1 to 25.

BRIEF DESCRIPTION OF THE DRAWINGS

In the appended drawings:

FIG. 5 shows the cyclic voltammetry curves at 0.05 mV $s^{-1}$ of the composite electrode of Example 2a.

DETAILED DESCRIPTION OF THE INVENTION

Figure 1:
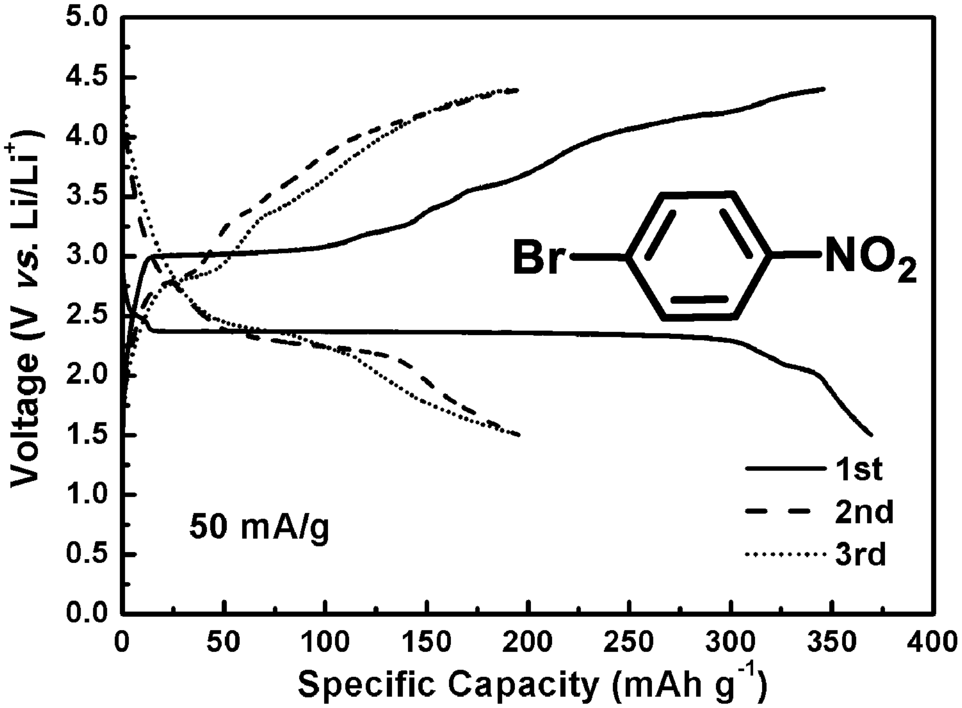
FIG. 1 shows the first three charge-discharge cycles of the composite electrode of Example 1a at 50 mA $g^{-1}$ (vs. $Li/Li^+$ anode).

Turning now to the invention in more details, there is provided the use of a nitro-substituted aromatic compound as an electrode material as well as the use of such a compound in the manufacture of an electrode. An electrode composite material comprising this compound is also provided. Finally, there is also provided an electrode comprising this nitro-substituted aromatic compound as well as a method of manufacturing an electrode comprising the step of forming the nitro-substituted aromatic compound into an electrode.

As shown in the Examples below, when used in metal-ion batteries, preferably Li-ion batteries, the electrode of the invention has a combination of high operating voltage (e.g. >2.0 V) and high specific capacities (e.g. >300 mAh $g^{-1}$). To the best of the inventors' knowledge, when used as electrode materials, some of nitro-substituted aromatic compounds of the invention have the highest specific capacity among organic electrode materials reported to date for application in alkali-ion batteries.

The nitro-substituted aromatic compound is of formula (I), (II), (III), or (IV):

(I)

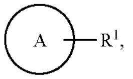

(II)

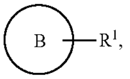

(III)

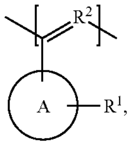

or (IV)

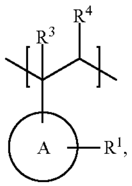

or a copolymer comprising repeat units of formula (III) and/or (IV), wherein:

A represents an arene or a heteroarene,

B represents an aromatic carbon allotrope, which is optionally doped with one or more heteroatoms, $R^1$ represents one or more -L-$NO_2$ substituents, $R^2$ represents =N—, =CH—, or =$CR^5$—, and $R^3$ and $R^4$ independently represents a hydrogen atom or $R^5$, wherein A and B are optionally further substituted by one or more $R^5$, wherein L represents a covalent bond or a linking group, and wherein each —$R^5$ independently represents $R^6$, —X, —$NH_2$, —$NR^6H$, —$NR^{62}$, —CN, —CHO, —COOH, —$COOR^6$, —$COO^-$ $M^+$, —OH, —$OR^6$, or —$O^-$ $M^+$ group, in which:

$R^6$ represents an alkyl, alkenyl, alkynyl, alkenylyl, aryl, or heteroaryl group, M represents a metal ion, and X represents a halogen atom.

In preferred embodiments, the nitro-substituted aromatic compound is of formula (I) or (IV), more preferably of formula (I).

The use, electrode material and electrode can comprise a single nitro-substituted aromatic compound according to the invention, or a mixture thereof or a composite thereof. Non-limiting examples of mixtures include mixtures comprising a nitro-substituted aromatic compound of formula (I) admixed with a nitro-substituted aromatic compound of formula (II) or (III) or (IV). Non-limiting examples of composites include composites comprising a carbon allotrope dispersed in a polymer matrix, i.e. a nitro-substituted aromatic compound of formula (II) dispersed in a matrix of a nitro-substituted aromatic compound of formula (III) or (IV).

The use, electrode material and electrode can comprise a nitro-substituted aromatic compound of the invention in admixture or forming a composite with an aromatic compound, in particular an aromatic compound that is not nitro-substituted, for example, a compound of formula (I'), (II'), (III'), or (IV'):

(I')

(II')

(III')

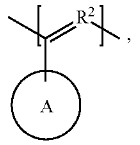

or (IV')

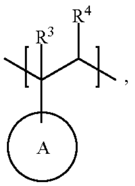

wherein A, B, $R_2$, $R_3$, and $R_4$ are as defined herein above and below (including preferred embodiments thereof).

Non-limiting examples of mixtures include mixtures comprising a nitro-substituted aromatic compound of formula (I) admixed with an aromatic (not nitro-substituted) compound of formula (II') or (III') or (IV'). Non-limiting examples of composites include composites comprising a carbon allotrope (not nitro-substituted) dispersed in a matrix of a nitro-substituted polymer, i.e. an aromatic compound of formula (II') dispersed in a matrix of a nitro-substituted aromatic compound of formula (III) and/or (IV).

The above nitro-substituted aromatic compound can also be used, e.g. in a mixture with a binder and a conducting material in the manufacture of the electrodes. Thus, there is also provided (as noted above) an electrode composite material comprising the nitro-substituted aromatic compound and optionally a binder and/or a conducting material.

The binder can be any binder known for use in electrodes. Non-limiting examples of binder includes Nafion® (sulfonated tetrafluoroethylene-based fluoropolymer-copolymer), polytetrafluoroethylene (PTFE) and polyvinylidene fluoride (PVDF). A preferred binder is Nafion®.

The conducting material can be any conducting material known for use in electrodes. Non-limiting examples of conducting material includes acetylene black, carbon nanotubes, graphene, and porous activated carbon. A preferred binder is acetylene black.

In embodiments, the composite has a nitro-substituted aromatic compound:conductive material:binder weight ratio ranging from about 30-100:0-50:0-15, preferably about 30-95:5-50:5-15, more preferably about 55-90:5-30:5-15, yet more preferably about 73-88:5-15:7-12, and most preferably the weight ratio is about 80:10:10.

In embodiments, the electrode comprises a current collector and the above composite disposed on the current collector. In preferred embodiments, the composite forms a film on the current collector.

In embodiments, the current collector is:

a metal foil or grid, which can be carbon-coated, a metal foam, a graphite plate, a carbon foam, a polymer film coated with a metal, or glass coated with a metal, wherein, in all cases, the metal is preferably gold (Au), platinum (Pt), titanium (Ti), copper (Cu), nickel (Ni), aluminum (Al), or stainless-steel. A preferred current collector is a metal foil, preferably an Al foil, and more preferably carbon-coated Al foil.

In embodiments, the metal foil may be from about 5 μm to about 50 μm thick. Furthermore, in embodiments, the current collector may have a finely texture surface to form an effective contact with the composite.

The electrode may be used in variety of electric devices. Non-limiting examples of such devices include:

- energy storage devices, such as a secondary battery (in particular lithium-ion batteries);
- electrochemical capacitors; and
- electrochemical capacitor display devices such as a field emission display (FED), a liquid crystal display (LCD), and an organic light-emitting diode (OLED).

Preferred devices in which the electrode of the invention is used include energy storage devices, preferably secondary batteries (e.g., metal batteries, including but not limited to Li, Na, K, Mg, Zn secondary batteries, and metal-ion batteries, including but not limited to Li-, Na-, K-, Mg-, Zn-, Ca-ion secondary batteries), more preferably alkali-ion secondary batteries, and most preferably lithium-ion secondary batteries. In such embodiments, the nitro group(s) of the nitro-substituted aromatic compound provide the redox-active functionality.

Substituent "A"

As noted above, in compounds of formulas (I), (I'), (III), (III'), (IV), and (IV'), A represents an arene or a heteroarene.

Herein, the terms "arene", "aryl", "heteroarene", and "heteroaryl" have their ordinary meaning in the art. For more certainty:

| Term | Definition |
|---|---|
| Arene | aromatic hydrocarbon presenting alternating double and single bonds between carbon atoms arranged in one or more rings. |
| Aryl | monovalent arene radical |
| heteroarene | arene wherein at least one of the carbon atoms forming the ring(s) is replaced by a heteroatom |
| heteroaryl | monovalent heteroarene radical |

Herein, a "heteroatom" is an atom other than a carbon atom or a hydrogen atom. Preferably, the heteroatom is oxygen, nitrogen, or sulfur, more preferably oxygen or nitrogen.

Herein, a "ring atom", such as a ring carbon atom or a ring heteroatom, refers to an atom that forms (with other ring atoms) a ring of a cyclic compound, such as a cycloalkyl, an aryl, etc.

It is to be noted that, unless otherwise specified, the ring(s) of the above groups can comprise between 4 and 8, preferably 5 or 6 ring atoms, more preferably 6 ring atoms.

Furthermore, each of the above compound may comprise more than one ring. In other words, they can be polycyclic. Polycyclic arenes are composed of multiple aromatic rings (organic rings in which the electrons are delocalized). Polycyclic arenes comprise fused aromatics. These are compounds that comprise two or more aromatic rings fused together by sharing two neighboring carbon atoms. The simplest such compounds are naphthalene, having two aromatic rings, and the three-ring compounds anthracene and phenanthrene. Polycyclic arenes also comprise compounds in which aromatic rings are attached to each other via a covalent bond or a carbon atom (bearing 0, 1, or 2 hydrogen atoms as needed depending on the number of aromatic rings to which it is attached).

For example, each of the above compound may comprise between 1 and 15 rings, preferably 1 to 5 rings, more preferably 1 to 3 rings, yet more preferably 1 or 2 rings, and more preferably 1 ring.

In preferred embodiments of the compounds of formulas (I), (I'), (III), (III'), (IV), and (IV'), the arene ring(s) comprise between 4 and 8, more preferably 5 or 6 ring atoms, and most preferably 6 ring atoms.

In more preferred embodiments, A represents one of the following arenes or heteroarenes,

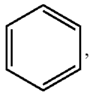,
benzene

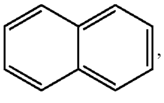,
naphthalene

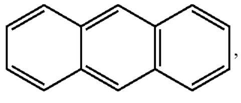,
anthracene

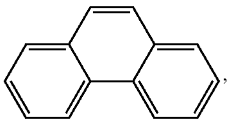,
phenanthrene

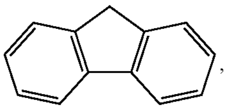,
fluorene

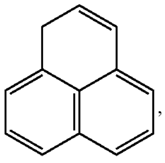,
phenalene

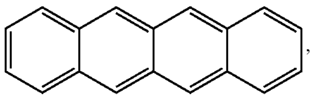,
tetracene

-continued

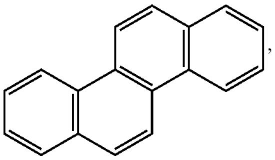, chrysene

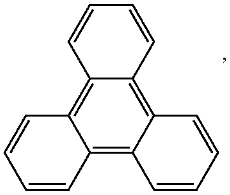, triphenylene

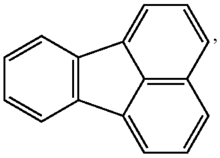, fluoranthene

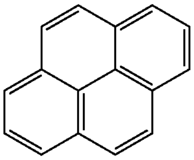, pyrene

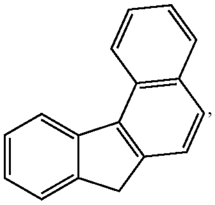, benzo[c]fluorene

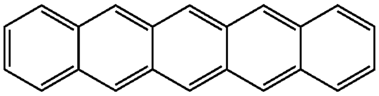, pentacene

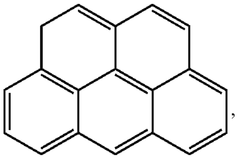,

Pentacyclo [13.3.1.0$^{5,18}$.0$^{8,17}$.0$^{11,16}$] nonadeca-1,3,5(18),7,9,11,13,15(19),16-nonaene

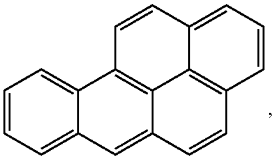, benzo[a]pyrene

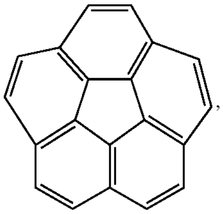, corannulene

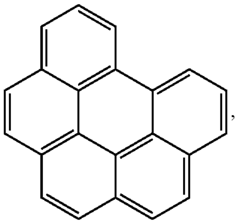, benzo[ghi]perylene

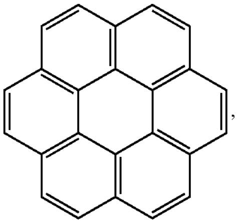, coronene

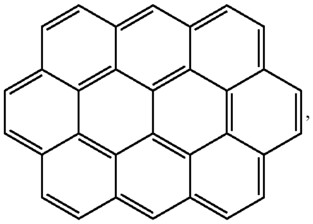, ovalene

-continued

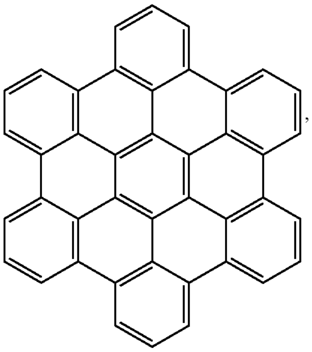, hexa-peri-hexabenzocoronene

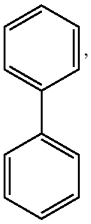, biphenyl

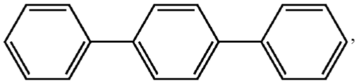, terphenyl

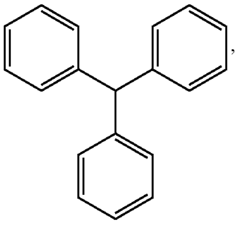, triphenylmethane

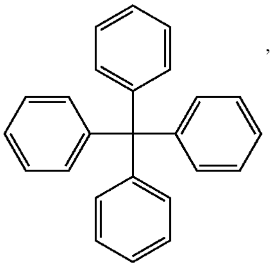, tetraphenylmethane

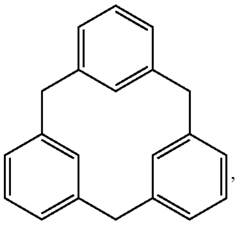, tetracyclo [13.3.1.1$^{3,7}$.1$^{9,13}$] henicosa-1(19),3,5,7(21),9,11,13(20),15,17-nonaene

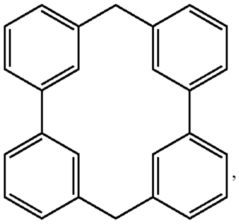, or pentacyclo [20.3.1.1$^{3,7}$.1$^{9,13}$.0$^{15,20}$] octacosa-1(26),3,5,7(28),9,11,13(27),15,17,19,22,24-dodecaene -continued

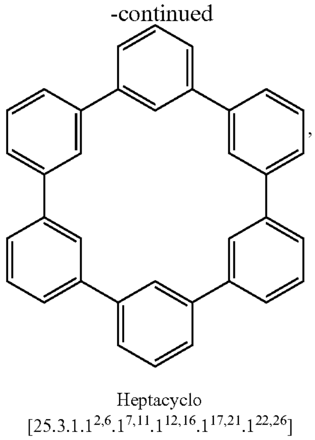

Heptacyclo
$[25.3.1.1^{2,6}.1^{7,11}.1^{12,16}.1^{17,21}.1^{22,26}]$
hexatriaconta-
1(31),2(36),3,5,7,9,11(35),
12(34),13,15,17,19,21(33),
22(32),23,25,27,29-
octadecaene and their corresponding heteroarenes, as well as:

, , 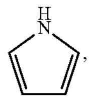, 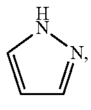, , 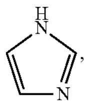, furan thiophene pyrrole pyrazole isoxazole imidazole

, , , 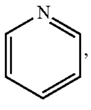, 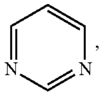, oxazole isothiazole thiazole pyridine pyrimidine

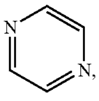, 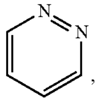, 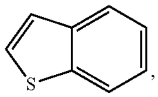, 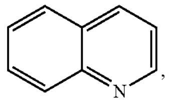, pyrazine pyridazine benzothiophene quinoline

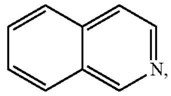, 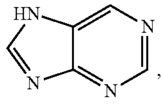, 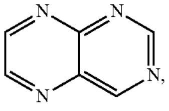, isoquinoline purine pteridine

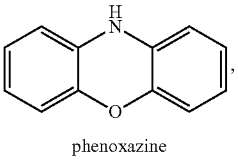, 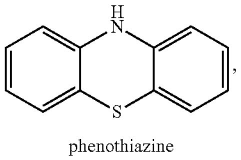, phenoxazine phenothiazine

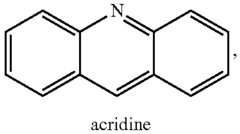, and 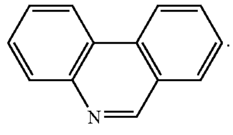.

acridine phenanthridine

Herein, an heteroarene which "corresponds to" an arene such as those listed above, is the arene in question in which one or more carbon ring atoms are replaced by heteroatoms.

In more preferred embodiments, A represents an arene, preferably benzene, naphthalene, biphenyl, triphenylmethane, fluorene, anthracene, pyrene, or pentacyclo$[13.3.1.0^{5,15}.0.0^{5,17}, 0.0^{11,16}]$nonadeca-1,3,5(18),7,9,11,13,15(19),16-nonaene; more preferably benzene, naphthalene, biphenyl, triphenylmethane, or fluorene, yet more preferably benzene or naphthalene, and most preferably benzene.

Substituent "$R_1$"

As noted above, in compounds of formulas (I) to (IV), $R^1$ represents one or more -L-$NO_2$ substituents (i.e. nitro group containing substituents).

It will be apparent that when $R^1$ represents more than one -L-$NO_2$ substituents, each substituent is attached on different ring carbon atoms of the arene (for compounds of formulas (I), (III), and, (IV)) or aromatic carbon allotrope (for compounds of formula (II)). Also, in such cases, each -L-$NO_2$ substituent is independent from the others. In other words, a given compound can bear two or more -L-$NO_2$ substituents, which may have the same or different L groups. Preferably, all -L-$NO_2$ substituents in a compound are the same.

In embodiments, especially of the compounds of formula (I), (III), and (IV), -L-$R^1$ represents 1 to 3 -L-$NO_2$ substituents; preferably 2 or 3 -L-$NO_2$ substituents, preferably 2 -L-$NO_2$ substituents.

In other embodiments, especially of the compounds of formula (II), -L-$R^1$ represents a number of -L-$NO_2$ substituents sufficient to functionalize the aromatic carbon allotrope, i.e. to alter its characteristics/performances.

As noted above, L represents a covalent bond or a linking group, preferably a covalent bond. Non-limiting examples of linking groups include alkylene, alkenylene, alkynylene, or alkenylylene, each of which being:

- optionally substituted with one or more $R^6$, —X, —$NH_2$, —$NR^6H$, —$NR^{62}$, —CN, —CHO, —COOH, —$COOR^6$, —$COO^-$ $M^+$, —OH, —$OR^6$, and/or —$O^-$ $M^+$, and
- optionally interrupted with one or more —O—, —$NR^6$—, —NH—, and/or —S—, wherein $R^6$ is as defined above.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. For more certainty:

| | |
|---|---|
| Saturated aliphatic hydrocarbons | |
| alkane | aliphatic hydrocarbon of general formula $C_nH_{2n+2}$ |
| alkyl | monovalent alkane radical of general formula —$C_nH_{2n+1}$ |
| alkylene (also called alkanediyl) | bivalent alkane radical of general formula —$C_nH_{2n}$— |
| Aliphatic hydrocarbons with double bond(s) | |
| alkene | aliphatic hydrocarbon, similar to an alkane but comprising at least one double bond |
| alkenyl | monovalent alkene radical, similar to an alkyl but comprising at least one double bond |
| alkenylene | bivalent alkene radical, similar to an alkylene but comprising at least one double bond |
| Aliphatic hydrocarbons with triple bond(s) | |
| alkyne | aliphatic hydrocarbon, similar to an alkane but comprising at least one triple bond |
| alkynyl | monovalent alkyne radical, similar to an alkyl but comprising at least one triple bond |
| alkynylene | bivalent alkyne radical, similar to an alkylene but comprising at least one triple bond |
| Aliphatic hydrocarbons with double and triple bond(s) | |
| alkenyne | aliphatic hydrocarbon, similar to an alkane but comprising at least one double bond and at least one triple bond |

-continued

| | |
|---|---|
| alkenynyl | monovalent alkenyne radical, similar to an alkyl but comprising at least one double bond and at least one triple bond |
| alkenynylene | bivalent alkenyne radical, similar to an alkylene but comprising at least one double bond and at least one triple bond |

It is to be noted that, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1, or preferably 2 carbon atoms.

Herein, a "group substituted with one or more A, B, and/or C" means that one or more hydrogen atoms of the group are replaced with substituents selected from A, B, and C. Of note, these substituents do not need to be identical: for example, one hydrogen atom may be replaced by A, while another may be replaced by B.

Herein, a "group interrupted with one or more A, B, and/or C" means that one or more A, B, and/or C groups are inserted between pairs adjacent carbon atoms of the group; for example, a butylene group ($—CH_2—CH_2—CH_2—CH_2—$) interrupted by —O— may be $—CH_2—CH_2—O—CH_2—CH_2—$. Preferably, only one of A, B orOC is inserted between any given pair of adjacent carbon atoms. However, when more than one pairs of adjacent carbon atoms are thus interrupted, the A, B, and C groups do not need to be identical: for example, one hydrogen atom may be replaced by A, while another may be replaced by B (for example a butylene group ($—CH_2—CH_2—CH_2—CH_2—$) interrupted by —O— and —NR— may be $—CH_2—NR—CH_2—O—CH_2—CH_2—$.

Substituent "$R_5$"

As noted above, in compounds of formulas (I), (I'), (II), (II'), (III), (III'), (IV), and (IV'), A and B are optionally substituted by one or more $R^5$ substituents. In embodiments, A and/or B are free of $R^5$ substituents. In other embodiments, A and/or B are so-substituted.

Preferred $R^5$ substituents among the list provided above include $—COO^- M^+$. In preferred such embodiments, M represents an alkaline metal ion, preferably a $Li^+$, $Na^+$, or $K^+$.

Compounds of Formulas (I)

In embodiments, the nitro-substituted aromatic compound is of formula (I).

In preferred embodiments, the nitro-substituted aromatic compound is:

a halonitrobenzene;
a dinitrobenzene;
a dinitrobenzoic acid;
a dinitrobenzoic acid salt;
a dinitronaphthalene;
a dinitronaphthalene;
a dinitrobiphenyl;
a tris(nitrophenyl)methane;
a dinitrofluorene;
a poly(nitrostyrene); or
nitrated polystyrene.

In more preferred embodiments, the nitro-substituted aromatic compound is:

1-bromo-4-nitrobenzene;
1,4-dinitrobenzene;
1,3-dinitrobenzene;
1,2-dinitrobenzene;
3,5-dinitrobenzoic acid;
3,5-dinitrobenzoic acid lithium salt;
3,5-dinitrobenzoic acid sodium salt;
3,5-dinitrobenzoic acid potassium salt;
1,5-dinitronaphthalene;
1,8-dinitronaphthalene;
4,4'-dinitrobiphenyl;
tris(4-nitrophenyl)methane;
2,7-dinitrofluorene;
poly(3-nitrostyrene); or
nitrated polystyrene.

In yet more preferred embodiments, the nitro-substituted aromatic compound is 1,4-dinitrobenzene; 3,5-dinitrobenzoic acid lithium salt; or nitrated polystyrene.

Compounds of Formulas (II) and (II')

In embodiments, the nitro-substituted aromatic compound is of formula (II).

As noted above, in formulas (II) and (II'), B represents an aromatic carbon allotrope, which is optionally doped with one or more heteroatoms. Preferably, the heteroatom(s) is(are) oxygen, nitrogen, or sulfur, more preferably oxygen or nitrogen.

Preferably, the allotropes are undoped.

Allotropy or allotropism is the property of some chemical elements to exist in two or more different forms, in the same physical state, known as allotropes of the elements. Carbon allotropes are well-known and include for example diamond, amorphous carbon, graphite, etc. Some of the allotropes of carbon are aromatic, such carbon allotropes are in fact akin to arenes and typically contain a very large number of fused aromatic rings. Aromatic carbon allotropes in B of formula (II) include, for example:

graphite,
graphene,
fullerenes,
carbon nanotubes,
carbon nanobuds (allotrope of carbon in which fullerene-like "buds" are covalently attached to the outer sidewalls of the carbon nanotubes),
carbon nanorods (carbon-based one-dimensional rod-like nanomaterials with diameters in the range of about 5 nanometers to about 100 nanometers and length-to-diameter aspect ratio of about 3 to 50),
carbon nanofibers (fibers about 5-500 nanometers in diameter with an atomic structure similar to that of graphite),
carbon nanosphere (carbon-based nanospheres with a diameter in the range of about 5-500 nanometers, which are often porous), and
activated carbon (which contains graphitic material as will be well-known of the skilled person), all of which optionally doped with one or more heteroatoms (preferably undoped). Preferred aromatic carbon allotropes in compounds of formulas (II) and (II') include carbon nanotubes, graphene, carbon nanofibers, and carbon nanospheres, all of which optionally doped with one or more heteroatoms (preferably undoped).

In nitro-substituted aromatic compound is of formula (II) and compounds of formula (II'), preferred $R^1$ groups are as described above.

Compounds of Formulas (III), (III'), (IV) and (IV')—Polymers and Copolymers

In embodiments, the nitro-substituted aromatic compound is of formula (III) or (IV).

Compounds of formula (III) or (IV) can be synthesized by polymerization of nitro-functionalized acetylenic monomers (for formula (III)) or vinyl monomers (for formula (IV)).

Compounds of formula (III) or (IV) can also be nitrated polymers prepared by nitrating aromatic acetylenic polymers (thus yielding polymers of formula (III)) or aromatic vinyl polymers (thus yielding polymers of formula (IV)).

Preferred compounds of formula (III) or (IV) include nitro-substituted polyphenylacetylene and nitro-substituted polystyrene, preferably nitro-substituted polystyrene. In embodiments, the nitro-substituted polystyrene can be produced by nitrating waste polystyrene.

In alternative embodiments, the nitro-substituted aromatic compound is a copolymer comprising repeat units of formula (III) and/or (IV).

Preferred repeat units of formula (III) or (IV) in these copolymers include nitro-substituted polyphenylacetylene and nitro-substituted polystyrene, preferably nitro-substituted polystyrene.

Non-limiting examples of other repeat units in such copolymers include repeat units of formula (III') and/or (IV'), other acetylenic repeat units, other vinyl monomer repeat units, including but not limited to styrenics, acrylates, methacrylates, and dienes. Preferred repeat units for copolymerization with repeat units of formula (III) and/or (IV) include phenylacetylene for formula (III), and styrene, divinylstyrene, methyl methacrylate, n-butyl acrylate, and 1,4-butadiene for formula (IV).

In compounds/repeat units of formula (III), (III'), (IV) and (IV') and copolymers comprising these repeat units, preferred A and $R^1$ are as described above.

In preferred compounds/repeat units of formula (III) and (III') and copolymers comprising these repeat units, $R^2$ represents =CH—.

In preferred compounds/repeat units of formula (IV) and (IV') and copolymers comprising these repeat units, both $R^3$ and $R^4$ represent hydrogen atoms.

Nitro-Substituted Aromatic Compounds

In some embodiments, the nitro-substituted aromatic compound is of formula (I), (II), (III), or (IV) as defined above are novel. Thus, there is provided herein the nitro-substituted aromatic compound is of formula (I), (II), (III), or (IV) as defined above.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, such as Formulas (I) to (IV), with various substituents ($R_1$, $R_2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it means plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—Representative Mononitro-Substituted Benzenes

1-Bromo-4-nitrobenzene was selected as a representative molecule to demonstrate the electrochemical performances of mononitro-substituted benzenes.

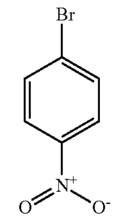

1-bromo-4-nitrobenzene
(1-Br-4-NB)

Example 1a —1-Bromo-4-nitrobenzene (1-Br-4-NB)

To prepare electrodes, 1-Br-4-NB (99%, Aldrich®) was composited with porous conductive carbon (carbon nanosphere with an average diameter of 20 nm) at a mass ratio of 40:60. In the procedure, 1-Br-4-NB was firstly dissolved in THF, followed with the addition of the prescribed amount of porous carbon. The mixture was stirred with a magnetic stirrer at 400 rpm at room temperature and was subsequently dried under vacuum. The solid mixture was then sealed, under vacuum, in a glass tube and then annealed at 160° C. for 18 h. After cooling to room temperature, the composite of 1-Br-4-NB with conductive carbon was obtained.

For electrode fabrication, a homogeneous slurry of the composite, Super-P® acetylene black, and binder (Nafion®) at a weight ratio of 80:10:10 in ethanol was prepared. The slurry was coated on a carbon-coated Al foil with a 1-Br-4-NB loading of 1.5~2 mg $cm^{-2}$, followed with drying at 65° C. for 5 h, then stored in a vacuum oven at 50° C. prior to use.

Electrochemical performances of the electrodes as cathodes were tested in CR2025-type coin cells assembled in Ar-filled glove box. The electrolyte employed contained 1.0 M LiTFSI in a binary solvent of DOL and DME (1:1 in volume). Lithium metal foil was used as the negative electrode and was physically separated from the cathodes with two sheets of Celgard® 2500 separators. The galvanostatic charge/discharge (GCD) tests were performed on a battery testing system (Land®, CT2001A, China).

Figure 2:
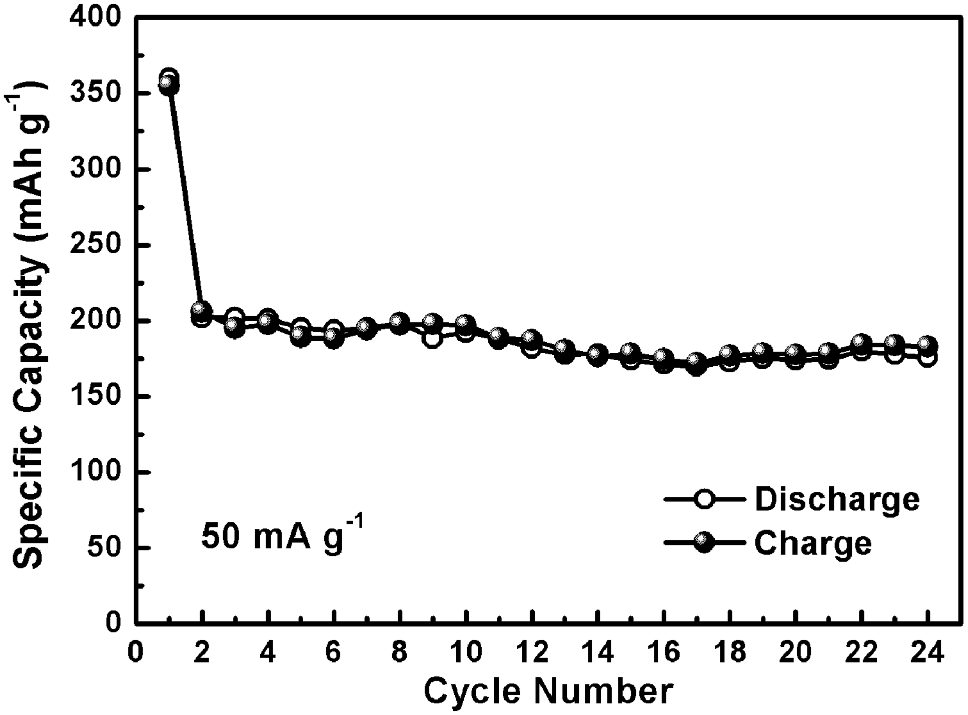
FIG. 2 shows the cyclic performance of the composite electrode of Example 1a at 50 mA $g^{-1}$.

FIGS. 1 and 2 show the electrochemical performance of 1-Br-4-NB composite electrode for Li-ion battery. FIG. 1 illustrates the voltage profiles of the first three charge-discharge cycles of the 1-Br-4-NB cathode at a mild current density of 50 mA $g^{-1}$. A discharge voltage plateau at 2.4 V is observed, along with a high initial capacity of 370 mAh $g^{-1}$, confirming its high capacity and high working voltage. FIG. 2 shows its cycling at 50 mA $g^{-1}$ with a terminal capacity of 170 mAh $g^{-1}$ obtained after 24 cycles, which is reasonable stable relative to the capacity of ca. 200 mAh $g^{-1}$ at the $2^{nd}$ cycle.

Example 2—Representative Dinitro-Substituted Benzenes

Dinitrobenzene (o, m and p), 3,5-dinitrobenzoic acid, and 3,5-dinitrobenzoic acid lithium, sodium and potassium salts were selected as representative molecules to demonstrate the electrochemical performances of mononitro-substituted benzenes. Their electrochemical performance as the organic cathode materials for alkali-ion (Li, Na and K ion) and alkaline earth metal (Zn, Mg and Al) ion batteries have been characterized as described below.

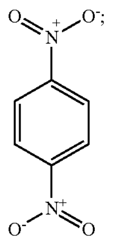

1,4-dinitrobenzene

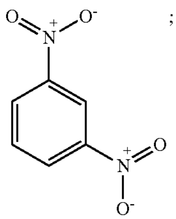

1,3-dinitrobenzene

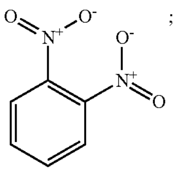

1,2-dinitrobenzene

-continued

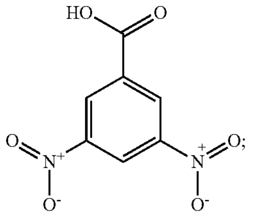

3,5-dinitrobenzoic acid

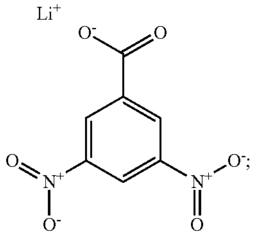

3,5-dinitrobenzoic acid lithium salt (also called lithium 3,5-dinitrobenzate)

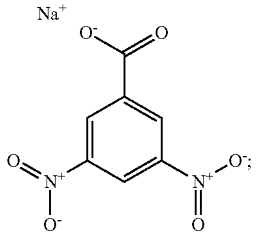

3,5-dinitrobenzoic acid sodium salt (also called sodium 3,5-dinitrobenzate)

and

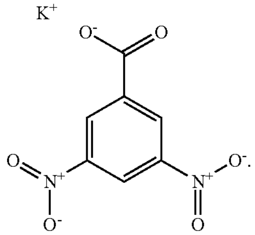

3,5-dinitrobenzoic acid potassium salt (also called potassium 3,5-dinitrobenzate)

Example 2a—1,4-Dinitrobenzene for Li-ion Batteries

A mixture of the pure 1,4-DNB, Super-P® acetylene black, and binder (Nafion®) at a weight ratio of 70:20:10 was mixed in ethanol to form a homogeneous slurry. Electrodes of pure 1,4-DNB were prepared by coating the slurry on the carbon-coated Al foil with a 1,4-DNB loading of 1.5~2 mg $cm^{-2}$, which were dried at 65° C. for 5 h and then in a vacuum oven at 50° C. prior to use.

1,4-Dinitrobenzene (1,4-DNB, 99%, Aldrich®) was dissolved in THF, followed with the addition of a prescribed amount of conductive porous carbon (carbon nanospheres with an average diameter of 20 nm; 1,4-DNB/C mass ratio=40:60). The dispersion was sonicated for 20 min and stirred with a magnetic stirrer at 400 rpm at room temperature, was subsequently dried under vacuum to isolate the solid mixture. The resulting solid mixture was then sealed, under vacuum, in a glass tube and annealed at 180° C. for 18 h. After cooling to room temperature, the composite of 1,4-DNB with porous carbon was obtained.

A mixture of the 1,4-DNB composite, Super-P® acetylene black, and binder (Nafion®) at a weight ratio of 80:10:10 was mixed in ethanol to form a homogeneous slurry. Electrodes of the 1,4-DNB composite were prepared by coating the slurry on the carbon-coated Al foil with a 1,4-DNB loading of 1.5~2 mg $cm^{-2}$, which were dried at 65° C. for 5 h and then in a vacuum oven at 50° C. prior to use.

Electrochemical performances of the electrodes were tested in CR2025-type coin cells assembled in an Ar-filled glove box. The electrolyte employed contained 1.0 M LiTFSI in a binary solvent of DOL and DME (1:1 in volume). Lithium metal foil was used as the negative electrode and was physically separated from the cathode with two sheets of Celgard® 2500 separators. GCD tests of the cells were performed on a battery testing system (Land®, CT2001A, China). Cyclic voltammetry (CV) measurements were recorded on a Metrohm® Autolab® PGSTAT128 N electrochemical workstation at a scan rate of 0.05 mV $s^{-1}$. Electrochemical impedance spectroscopy (EIS, Metrohm® Autolab® PGSTAT128) measurements were carried out from 100 kHz to 0.01 Hz with an ac amplitude of 5 mV.

Figure 3:
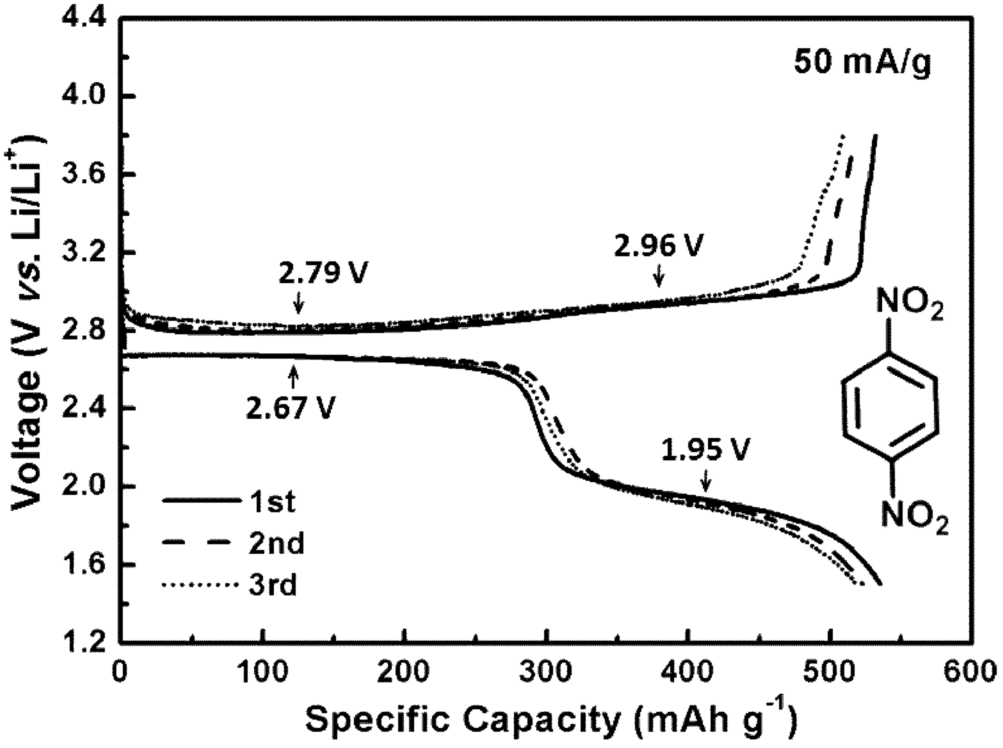
FIG. 3 shows the first three charge-discharge cycles of the pure 1,4-DNB electrode of Example 2a at 50 mA $g^{-1}$ (vs. $Li/Li^+$ anode).
Figure 4:
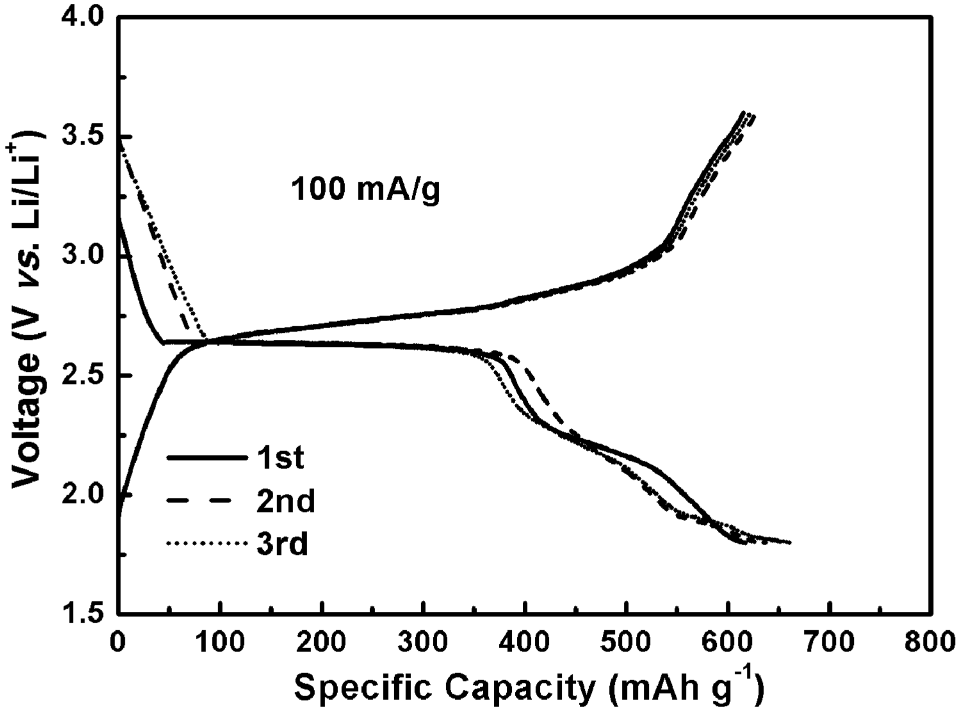
FIG. 4 shows the first three charge-discharge cycles of the composite electrode of Example 2a at 100 mA $g^{-1}$ (vs. $Li/Li^+$ anode) for Li-ion battery.
Figure 5:
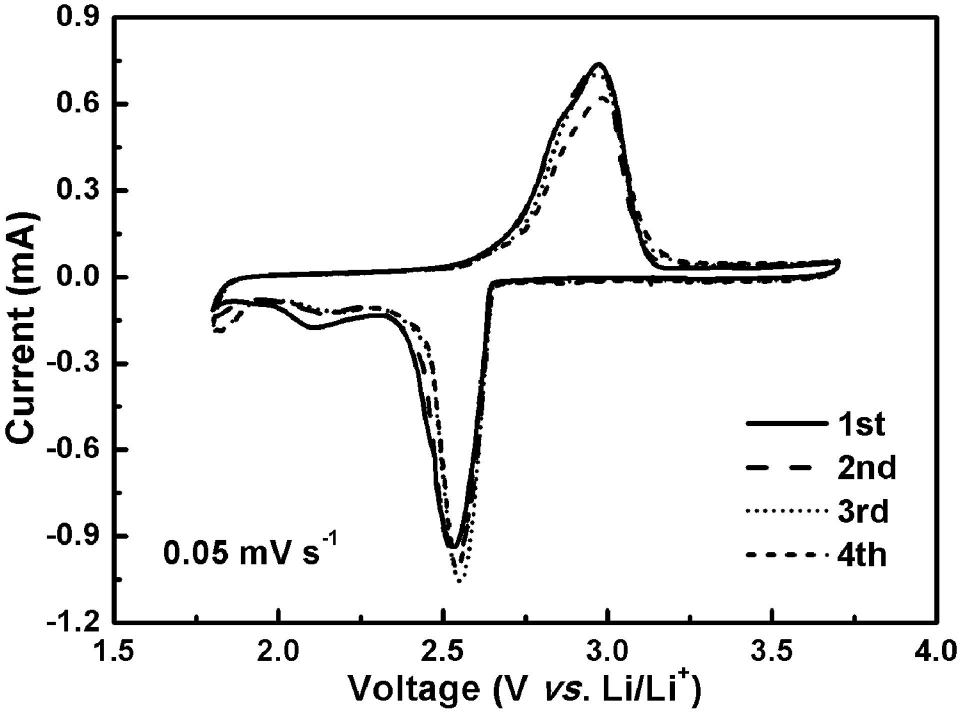
Figure 6:
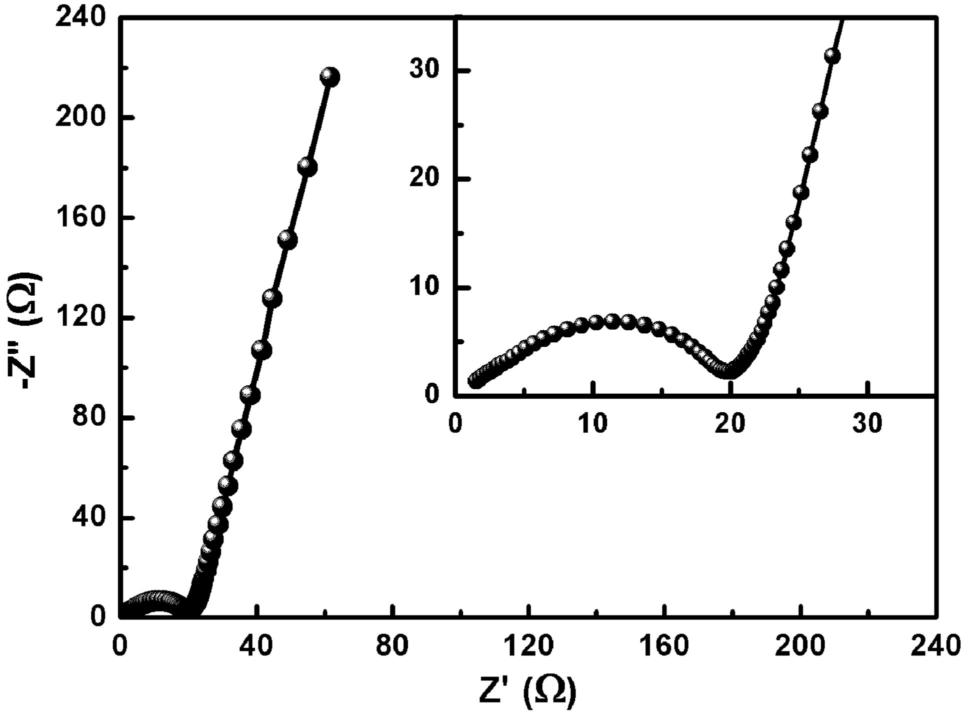
FIG. 6 shows the Nyquist plot of the composite electrode of Example 2a, with a closer view of the first part of the plot in the inset.
Figure 7:
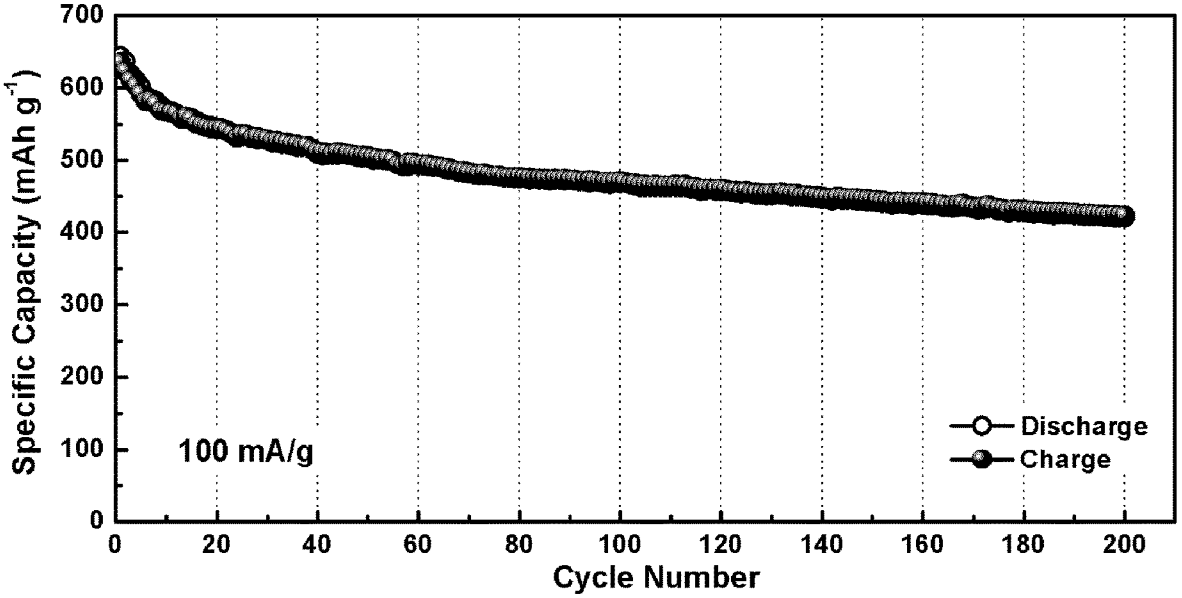
FIG. 7 shows the cyclic performance of the composite electrode of Example 2a at 100 mA $g^{-1}$.
Figure 8:
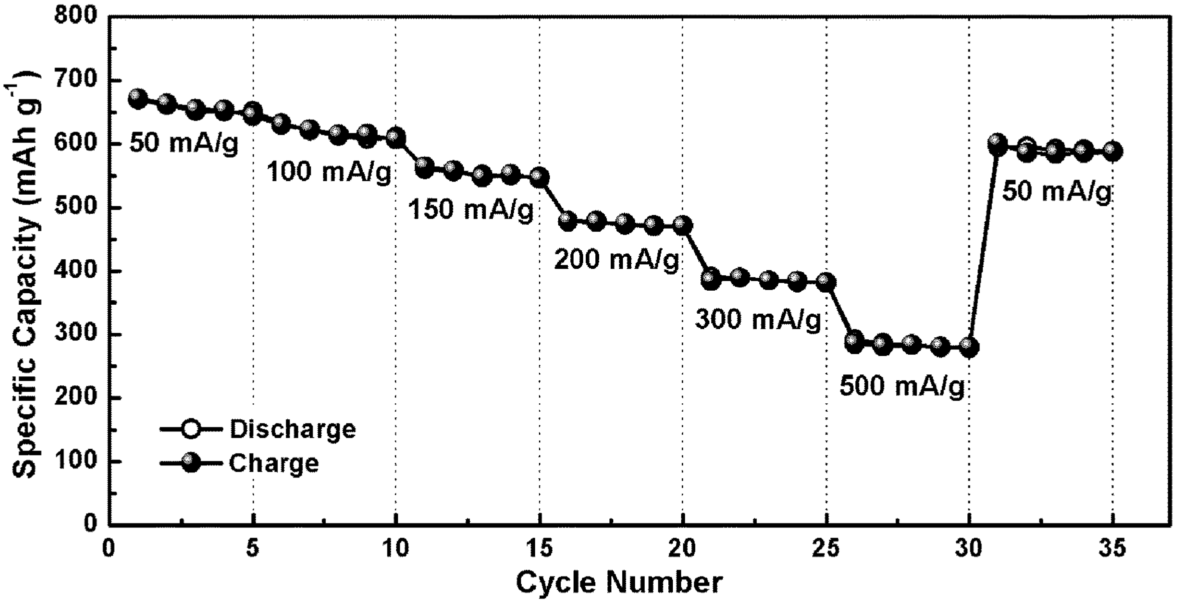
FIG. 8 shows the rate performance of the composite electrode of Example 2a at various current densities.

FIG. 3 show the electrochemical performance of pure 1,4-DNB cathode. Distinct voltage plateaus at 2.67 V and 1.95 V in the discharge curves, while 2.79 V and 2.96 V in the charge curves, are observed, along with high specific capacities exceeding 500 mAh $g^{-1}$ in the first three cycles at 50 mA $g^{-1}$. FIGS. 4-8 show the electrochemical performance of the 1,4-DNB composite cathode. In the voltage curves shown in FIG. 4, distinct voltage plateaus at 2.6 V, 2.2 V, and 1.8 V, respectively, are observed, along with high specific capacities exceeding 600 mAh $g^{-1}$ in the first three cycles at 100 mA $g^{-1}$. In the CV curves (FIG. 5), distinct reduction and oxidation peaks are observed ca. 2.54 and 2.9 V, respectively, with a low polarization of ca. 0.36 V. The overlapped CV curves in the repeated cycles demonstrate the good reversible electrochemical reactions of the cathode. EIS test (FIG. 6) shows the low equivalent series resistance of only 1Ω and a charge transfer resistance of about 18Ω, confirming its high electronic conductivity. Cycling test at 100 mA $g^{-1}$ for 200 cycles (FIG. 7) shows its high stability and long life, with a terminal capacity of 420 mAh $g^{-1}$ and a low capacity decay rate of 0.17%. From the rate capability test (FIG. 8), a significant specific capacity of around 300 mAh $g^{-1}$ is retained for the composite electrode even at a high current density of 500 mA $g^{-1}$, confirming its excellent rate performance.

Figure 9:
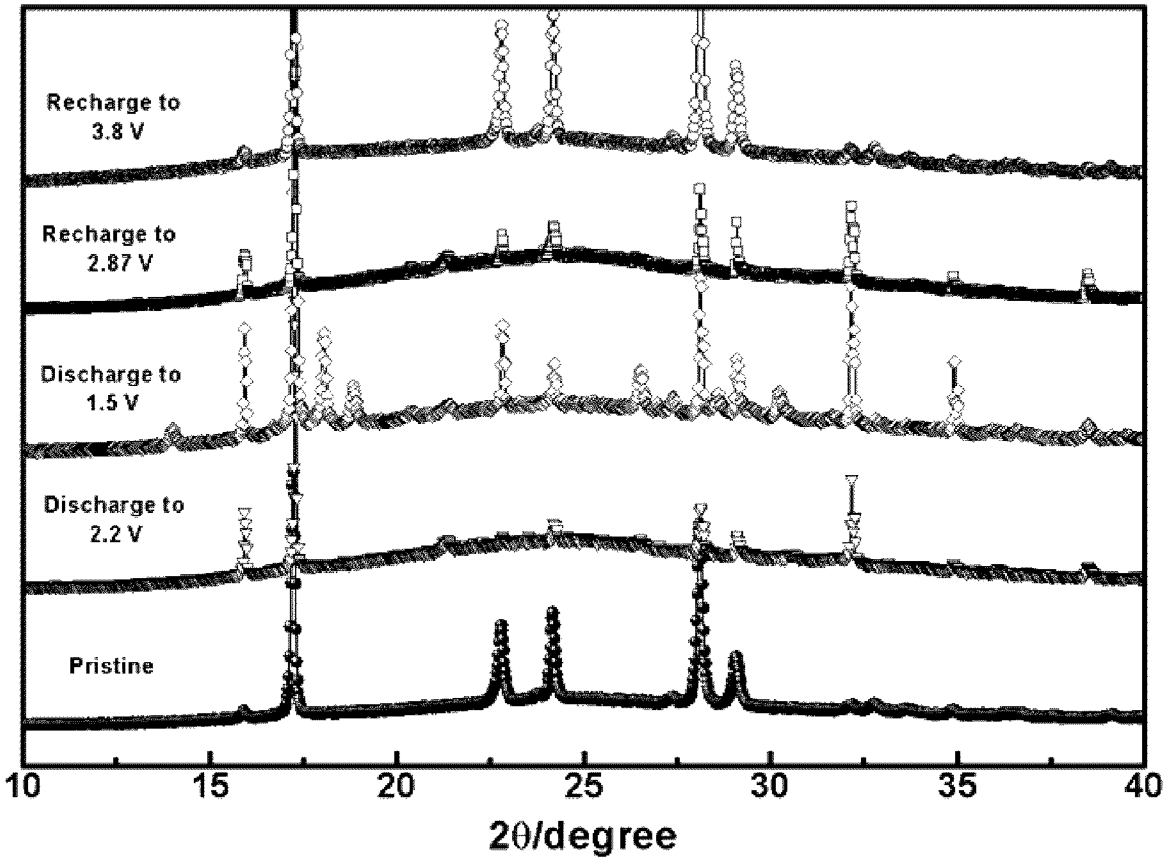
FIG. 9 shows the ex-situ XRD patterns of Example 2a collected at different voltage states during the first discharge/charge.

Ex situ characterizations were performed on the pure 1,4-DNB electrode to verify its electrochemical reversibility and to elucidate the redox mechanism. FIG. 9 shows the ex-situ XRD measurements of pure 1,4-DNB electrode at different voltage states (pristine prior to cycling, discharged to 2.2 V, discharged to 1.5 V, recharged to 2.87 V and recharged to 3.8 V) in the first discharge and charge processes. The discharge curve is divided into two nearly equal plateaus at 2.67 and 1.95 V (FIG. 3), corresponding to the insertion of $Li^+$ ions through two two-phase reaction steps. Prior to cycling, all peaks from the initial pristine electrode are well indexed to the monoclinic crystalline structure of pure 1,4-DNB. When discharged to 2.2 V (i.e., at the completion of the first plateau at 2.67 V), the formation of the new $Li_2C_6H_4N_2O_4$ dianion intermediate phase can be clearly identified. After the further discharge to 1.5 V (i.e., at the completion of the $2^{nd}$ discharge plateau at 1.95 V), the intermediate $Li_2C_6H_4N_2O_4$ phase transforms into the final tetraanion product, $Li_4C_6H_4N_2O_4$ phase. When recharged to 2.87 V (i.e., the central point of the charge curve), the XRD pattern reverts nicely back to that of the $Li_2C_6H_4N_2O_4$ dianion phase at 2.2 V with identical characteristic peaks observed, confirming solidly the transformation of the tetraanion phase back to the intermediate dianion phase. Upon the charge back to 3.8 V, the XRD pattern is fully converted back to the pristine neutral 1,4-DNB phase with the complete disappearance of all new peaks seen above, confirming the complete lithium extraction. These ex-situ XRD results verify the two-step two-phase reaction involved in both the discharge and charge processes.

Figure 10:
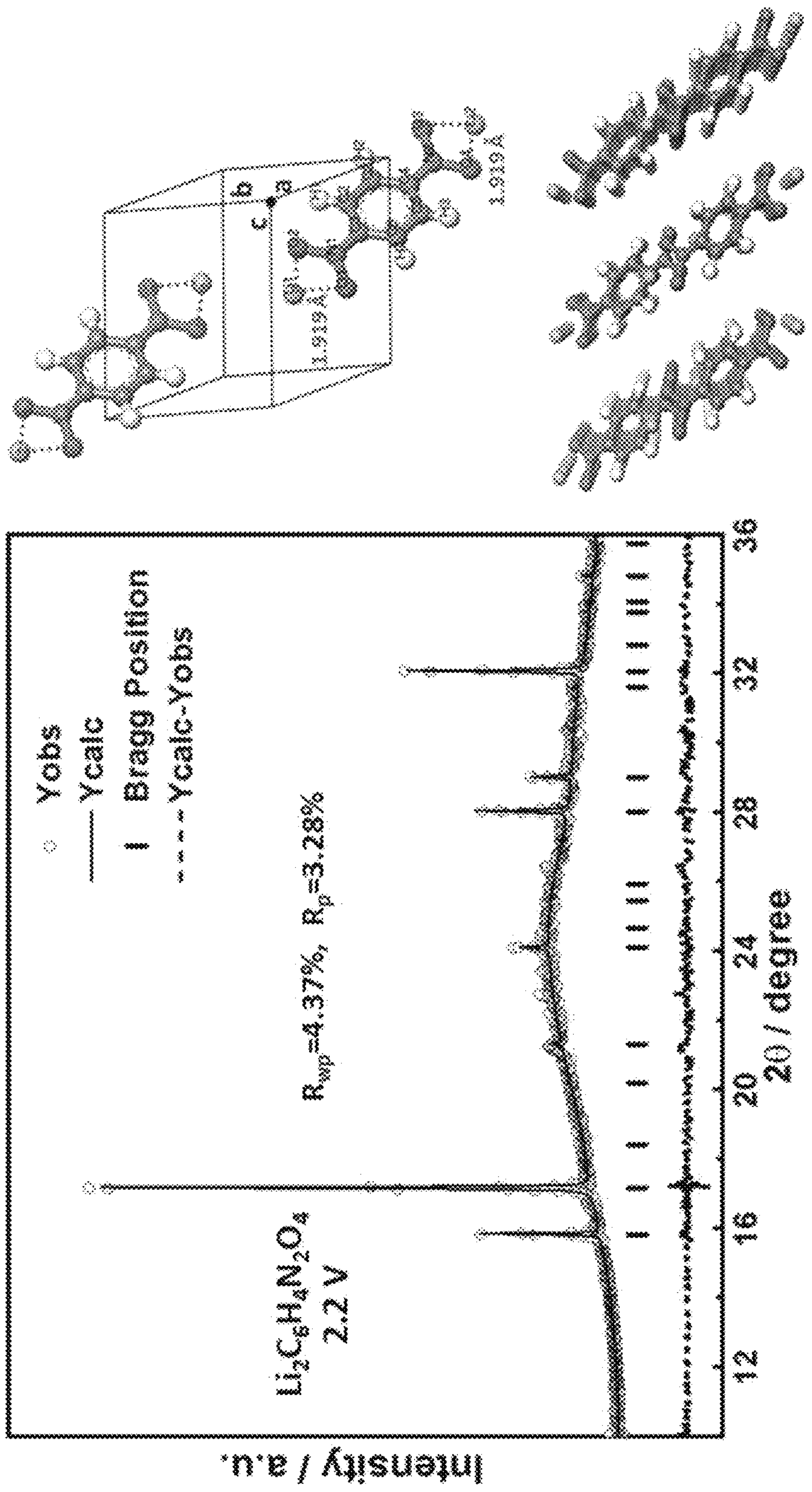
FIG. 10 shows the refined XRD patterns and corresponding crystal structures of Example 2a discharged to 2.2 V ($Li_2C_6H_4N_2O_4$).
Figure 11:
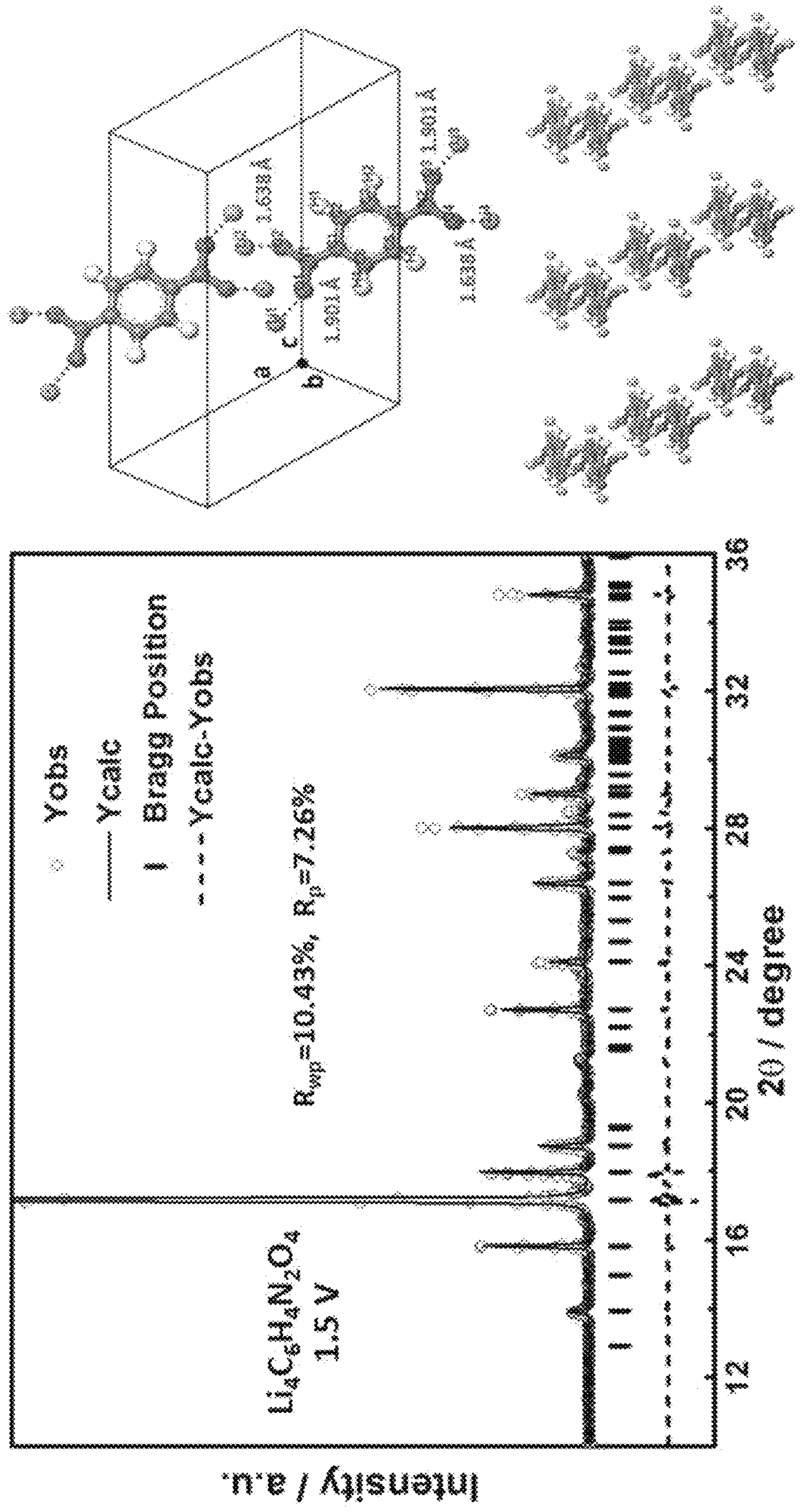
FIG. 11 shows the refined XRD patterns and corresponding crystal structures of Example 2a discharged to 1.5 V ($Li_4C_6H_4N_2O_4$).

FIGS. 10 and 11 show the structures of the intermediate dianion $Li_2C_6H_4N_2O_4$ phase and tetraanion $Li_4C_6H_4N_2O_4$ phase generated upon lithium insertion, respectively, which have been resolved from their ex-situ XRD patterns by using a similar direct space approach. Both two phases adopt the centrosymmetric triclinic system and the $P_{-1}$ space group. The resolved structures perfectly fit the diffraction patterns with excellent Rietveld refinement agreement factors. For the $Li_2C_6H_4N_2O_4$ phase (FIG. 10), the unit cell confirms that each nitro group acquires one Li atom, with two Li atoms inserted into each 1,4-DNB molecule after the first two-phase reaction during the discharge. Upon the second two-phase reaction, the unit cell of $Li_4C_6H_4N_2O_4$ phase (FIG. 11) demonstrates that each nitro group acquires an additional lithium atom with four lithium atoms in one molecule.

Figure 12:
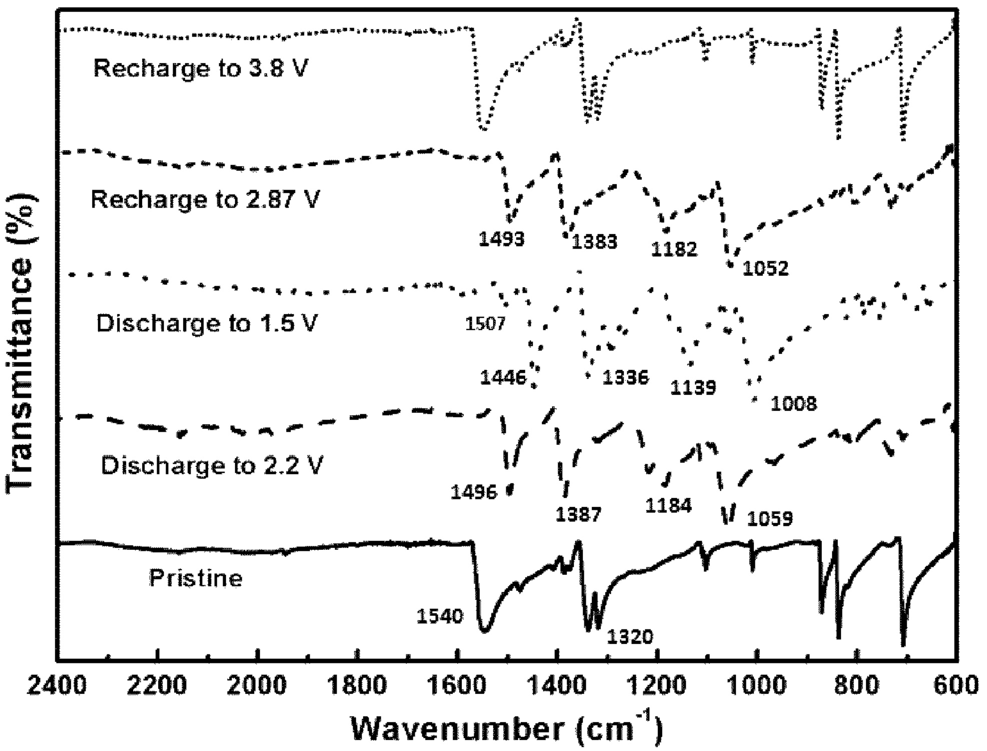
FIG. 12 shows the ex-situ FTIR spectroscopy of Example 2a collected at different voltage states during the first discharge/charge.
Figure 13:
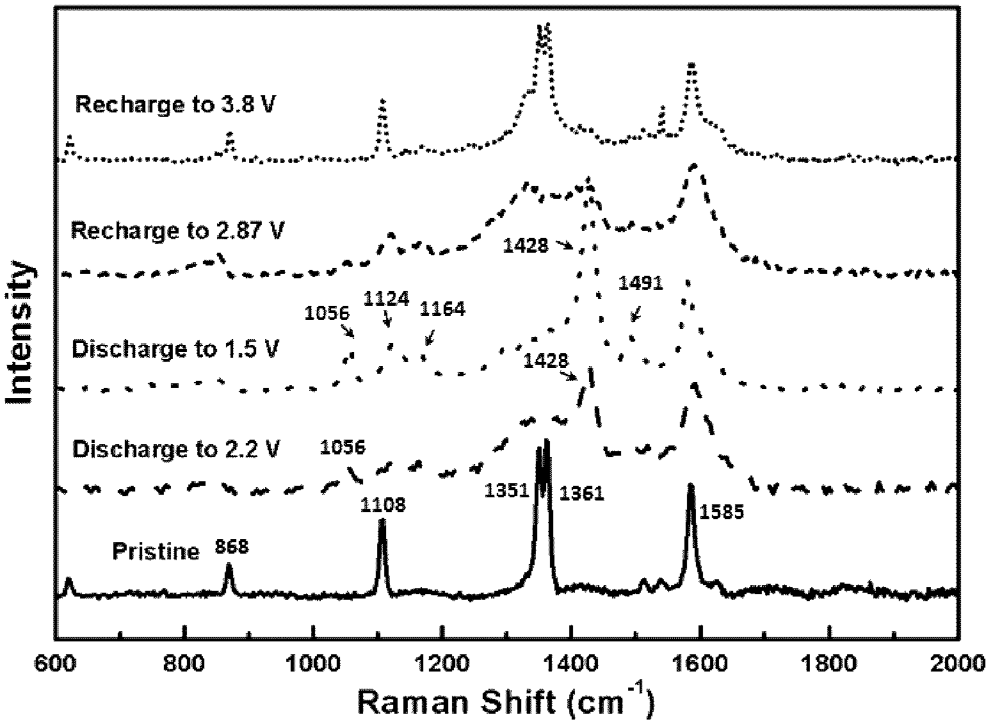
FIG. 13 shows the ex-situ Raman spectroscopy of Example 2a collected at different voltage states during the first discharge/charge.

FIGS. 12 and 13 show the ex-situ FTIR and Raman spectroscopy of pure 1,4-DNB electrode at different voltage states (pristine prior to cycling, discharged to 2.2 V, discharged to 1.5 V, recharged to 2.87 V and recharged to 3.8 V) in the first discharge and charge processes. Both FTIR (FIG. 12) and Raman (FIG. 13) spectra of the pristine sample show the corresponding characteristic bands of pure 1,4-DNB. In the sample discharged to 2.2 V, the characteristic nitro stretching FTIR bands at 1540 and 1320 $cm^{-1}$ disappear whereas new bands at 1496, 1387, 1184 and 1059 $cm^{-1}$ appear, which should be attributed to the lithiated nitro dianion intermediate. In its Raman spectra, all bands of 1,4-DNB except the C—C stretching band at 1585 $cm^{-1}$ disappear whereas a new band at 1428 $cm^{-1}$ attributable to lithiated nitro groups appears along with another weaker new band at 1056 $cm^{-1}$. Meanwhile, the C—C stretching band at 1585 $cm^{-1}$ gets significantly broadened, compared to the pristine sample, upon the reductive lithiation. Upon the second step of lithiation to 1.5 V, the set of FTIR bands seen above in the intermediate dianion is right-shifted to 1446, 1336, 1139 and 1008 $cm^{-1}$, respectively. The new Raman bands at 1506, 1124, 1164 and 1428 $cm^{-1}$ get intensified with sharper signals along with another new band at 1491 $cm^{-1}$ observed. These indicate that the lithiated tetraanion has the similar Raman bands as the lithiated dianion. Upon recharge to 2.87 V, FTIR and Raman bands characteristic of the lithiated dianion are recovered, confirming the partial delithiation of the lithium tetraanion to regenerate the lithiated dianion. After the full recharge to 3.8 V, all the characteristic FTIR and Raman bands for neutral 1,4-DNB are nicely restored with the disappearance of the bands for lithiated nitro groups, confirming the reversible recovery of 1,4-DNB molecular structure during the discharge-charge cycle.

Figure 14:
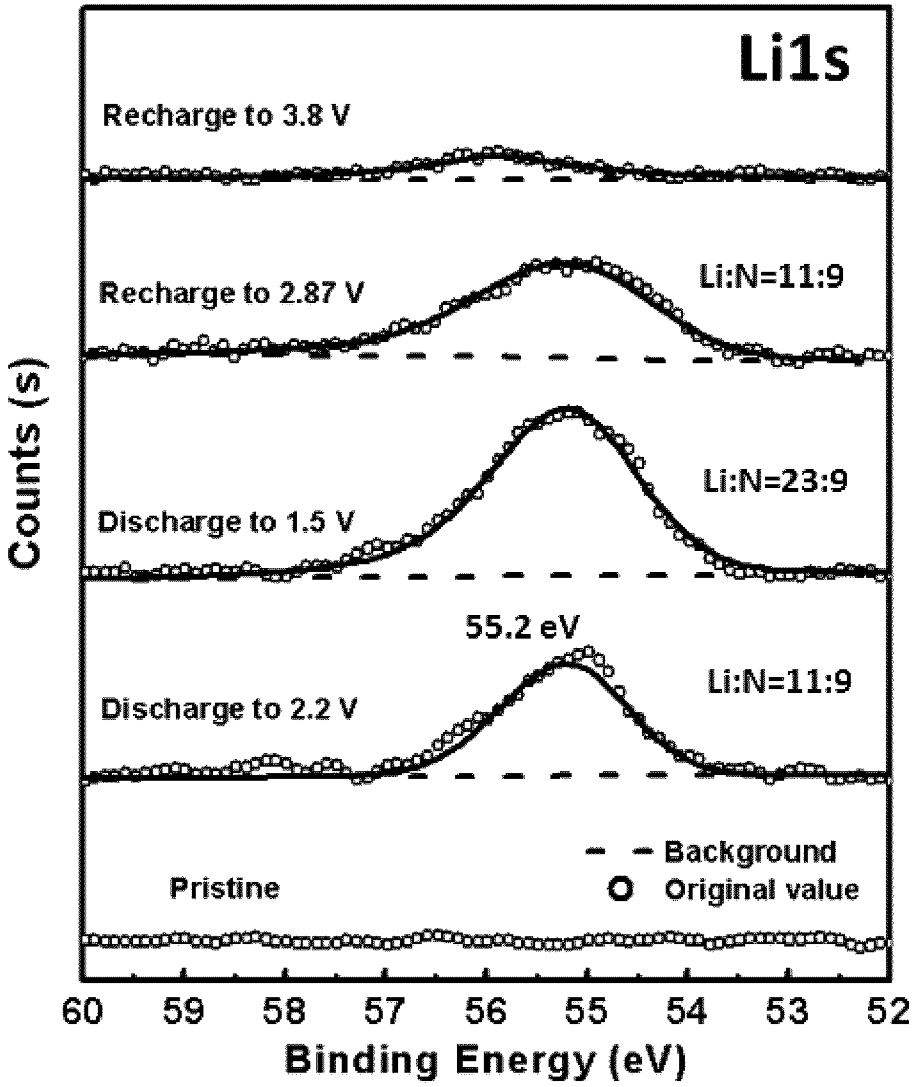
FIG. 14 XPS Li1s core level spectra of Example 2a collected at different voltage states during the first discharge/charge.

FIG. 14 show the XPS core spectra of Li elements in the samples at different lithiation/delithiation stages. Compared to the pristine sample without containing any Li species, strong Li1s signals are seen in the samples discharged to 2.2/1.5 V and recharged to 2.87 V. The relative intensity of Li1s in reference to N1s signal increases from 11/9 to 23/9 upon the deepening of discharge from 2.2 to 1.5 V due to enhanced lithiation and then decreases back to 11/9 upon recharge to 2.87 V by delithiation. The Li/N molar ratios are close to the theoretical ratios of 1/1, 2/1, and 1/1, respectively. The results also confirm the two-electron transfer with the insertion of two lithium ions per 1,4-DNB molecule in the first-step reaction at 2.2 V and four-electron transfer with the insertion of four lithium ions after the second-step reaction at 1.5 V during discharge. The reversed reactions take place in the recharge, with two lithium ions extracted per 1,4-DNB molecule upon recharge to 2.87 V. After recharge to 3.8 V, the Li1s signal nearly completely disappears, with only a trace intensity possibly resulting from the minute amount of electrolyte adsorbed on the particle surface.

Figure 15:
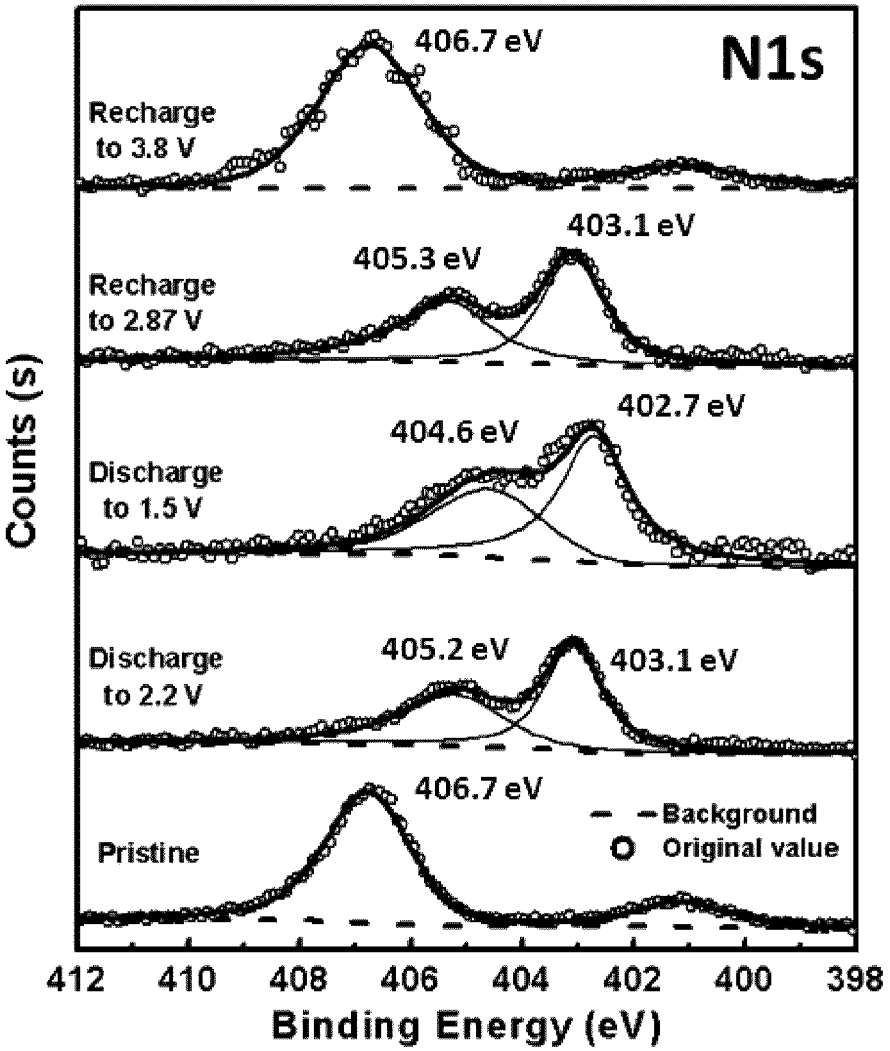
FIG. 15 XPS N1s core level spectra of Example 2a collected at different voltage states during the first discharge/charge.
Figure 16:
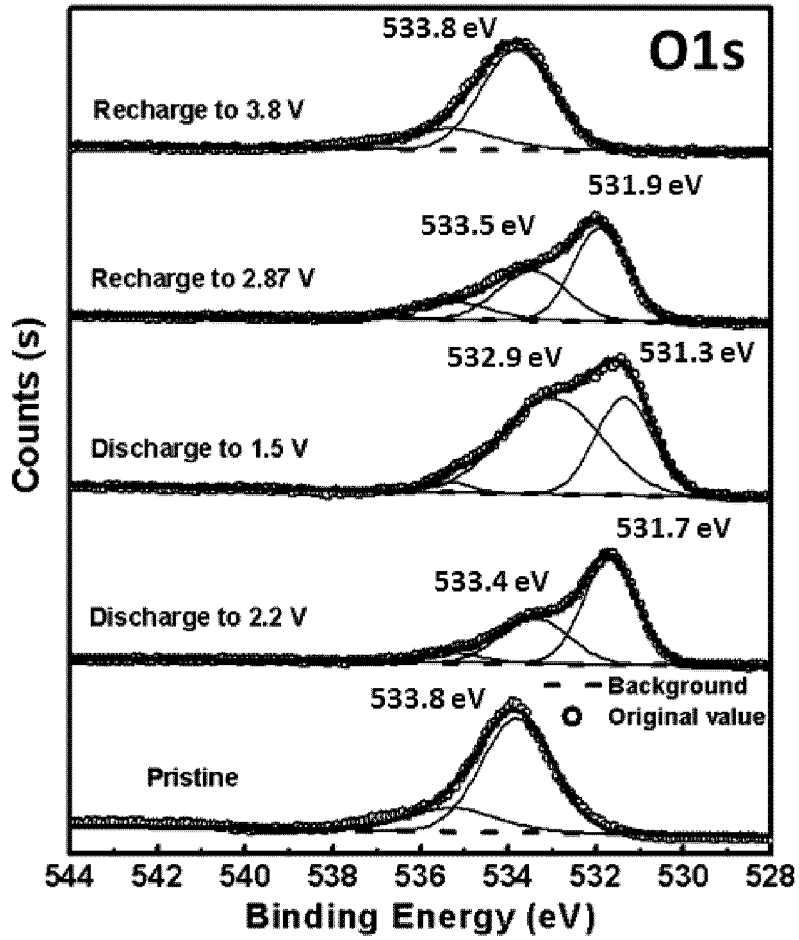
FIG. 16 XPS O1s core level spectra of Example 2a collected at different voltage states during the first discharge/charge.

FIGS. 15 and 16 show the XPS core spectra of N and O elements in the samples at different lithiation/delithiation stages. The N1s spectrum (FIG. 15) of the pristine sample show a primary peak at 406.7 eV and a weak satellite peak at 401.2 eV from nitro groups; its O1s spectrum (FIG. 16) shows the primary peak at 533.8 eV. When discharged to 2.2 V, both N1s and O1s signals show two deconvoluted peaks at 405.2 and 403.1 eV for the former, and 533.4 and 531.7 eV for the latter, which should be attributed to the lithiated nitro dianion. Upon the second step of lithiation to 1.5 V, slight right shifts of the deconvoluted N1s (404.6 and 402.7 eV) and O1s peaks (532.9 and 531.3 eV) are observed, indicating that the lithiated tetraanion product has slightly lowered binding energies for N1s and O1s than the dianion intermediate. When recharged to 2.87 V, the N1s and O1s peaks shift back to the binding energies for the lithiated dianion. After recharge to 3.8 V, the N1s and O1s peaks for neutral nitro groups are fully restored, with the complete disappearance of the signals for lithiated nitro groups.

Figure 17:
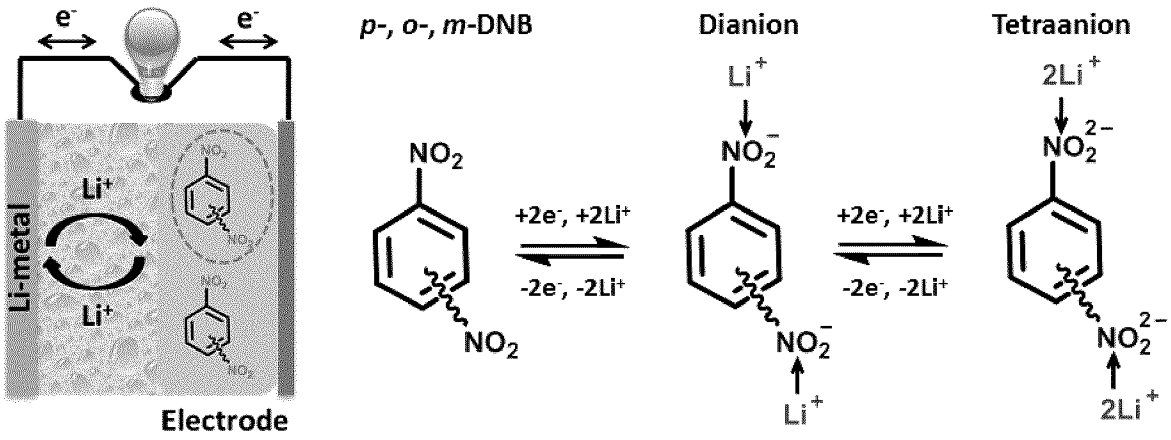
FIG. 17 Electrochemical redox reaction mechanism for Example 2a and 2f during the discharge-charge cycle.
Figure 18:
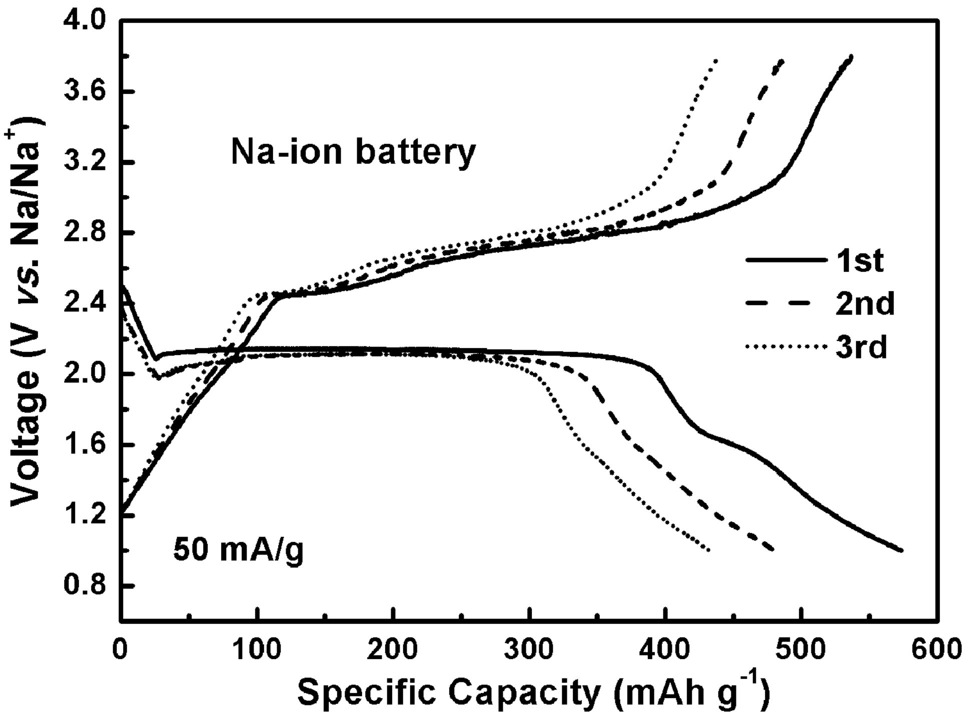
FIG. 18 shows the first three charge-discharge cycles of the 1,4-DNB composite electrode of Example 2b at 50 mA $g^{-1}$ (vs. $Na/Na^+$ anode.
Figure 19:
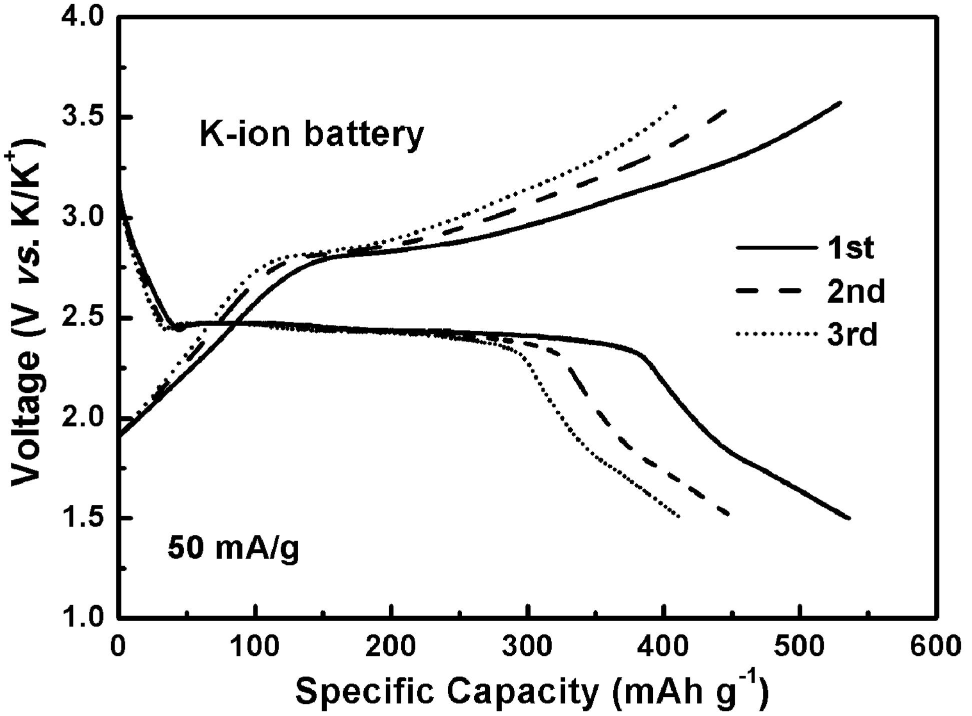
FIG. 19 shows the first three charge-discharge cycles of the 1,4-DNB composite electrode of Example 2b at 50 mA $g^{-1}$ (vs. $K/K^+$ anode.
Figure 20:
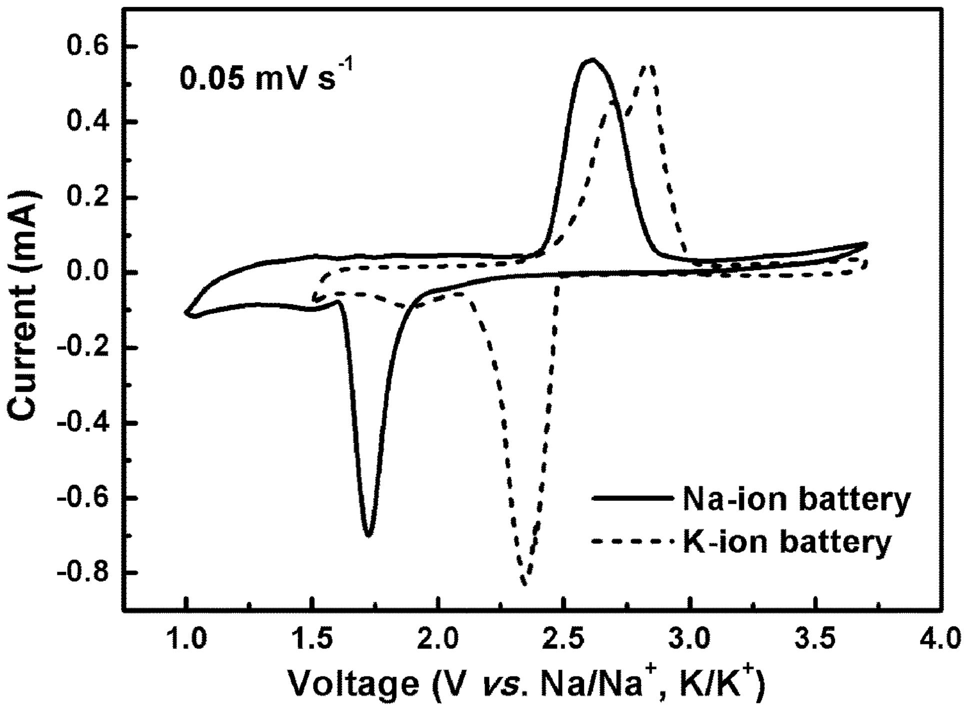
FIG. 20 shows the cyclic performance of the 1,4-DNB composite electrode of Example 2b in Na-ion and K-ion batteries at 0.05 mV $s^{-1}$.
Figure 21:
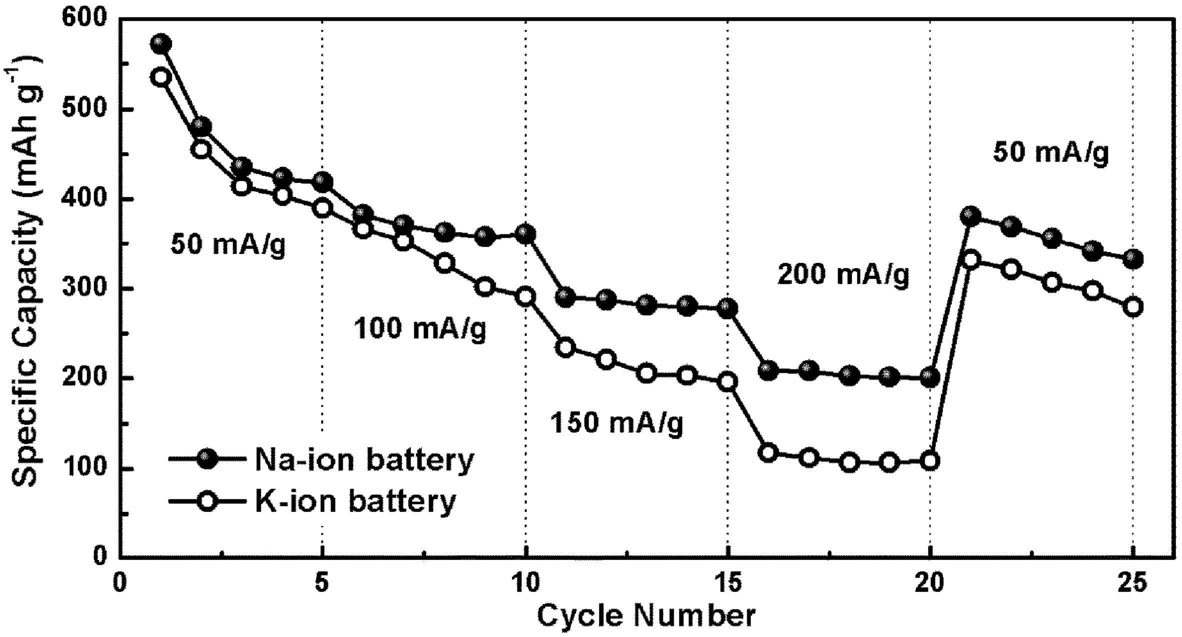
FIG. 21 shows the rate performance at various current densities (50 to 200 mA $g^{-1}$) of the 1,4-DNB composite electrode of Example 2b in Na-ion and K-ion batteries.

FIG. 17 show the proposed four-electron transfer mechanism through the two successive two-phase reactions in both the discharge and charge processes for Example 2a (1,4-DNB) and Example 2f (1,2-DNB and 1,3-DNB).

Example 2b—1,4-Dinitrobenzene for Na and K-ion Batteries

Electrochemical performances of 1,4-DNB composite cathodes for Na- and K-ion batteries were also tested. CR2025-type coin cells were assembled with the 1,4-DNB composite cathode and sodium or potassium metal foil used as the negative electrode, which was physically separated from the cathode with a glass fiber separator. The electrolyte employed contained 1.0 M NaTFSI or KTFSI in a binary solvent of DOL and DME (1:1 in volume).

Figure 22:
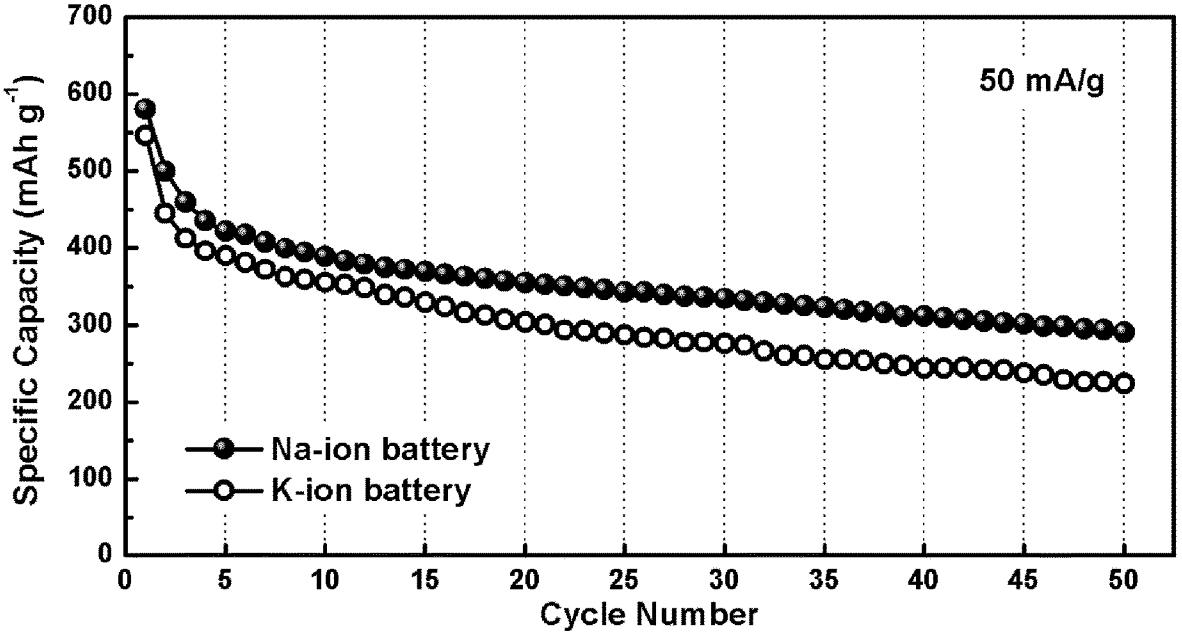
FIG. 22 shows the cycle performance at 50 mA $g^{-1}$ of the 1,4-DNB composite electrode of Example 2b in Na-ion and K-ion batteries.

FIGS. 18-22 show the electrochemical performance of 1,4-DNB cathodes for Na- and K-ion batteries. The initial specific capacities exceed 500 mAh $g^{-1}$ at the current density of 50 mA $g^{-1}$ for both Na- (FIG. 18) and K-ion (FIG. 19) batteries, along with stable voltage plateaus at around 2.2 and 2.5 V, respectively. The CV curves (FIG. 20) further demonstrate their different working voltages. The rate performance curves (FIG. 21) suggest their strong potential of 1,4-DNB for the application as cathode material in Na- and K-ion batteries. FIG. 22 plots the cyclic performance curves of 1,4-DNB cathodes in both Na- and K-ion batteries at 50 mA $g^{-1}$. Although an obvious capacity decay is observed in both Na- and K-ion batteries (FIG. 22), the observed performances are very promising and optimization work will very likely improve the cyclic stability.

Example 2c—1,4-Dinitrobenzene for Zn-ion Batteries 1,4-DNB was also used and evaluated as the cathode material for Zn-ion batteries. For the cathode fabrication, the homogeneous dispersion of the above prepared 1,4-DNB/porous conductive carbon composite, Super-P® acetylene black, and binder (PVDF) at a weight ratio of 80:10:10 in NMP was coated onto carbon paper at 1,4-DNB loading of 1.5~2 mg $cm^{-2}$. All the electrodes were dried at 65° C. for 5 h then in a vacuum oven at 50° C. CR2025-type coin cells were assembled with the 1,4-DNB composite cathode and zinc metal foil as the anode, which were separated with a glass fiber separator. The electrolyte employed contained 0.2 M $Zn(CF_3SO_3)_2$ in DMSO as solvent.

Figure 23:
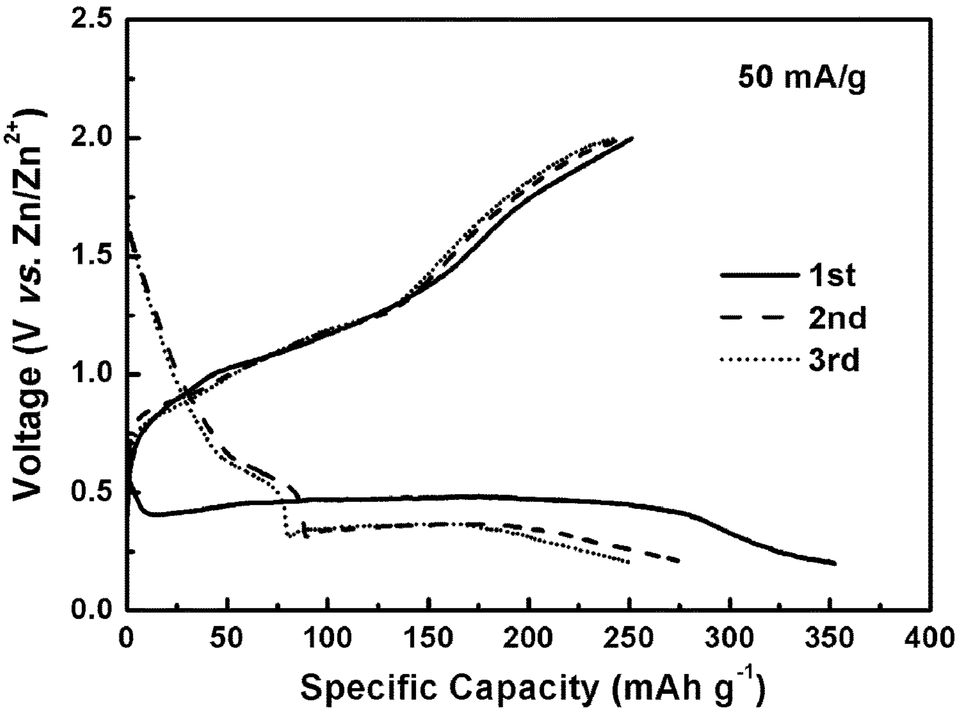
FIG. 23 shows the first three charge-discharge cycles of the 1,4-DNB composite electrode of Example 2c at 50 mA $g^{-1}$ (vs. $Zn/Zn^{2+}$ anode).
Figure 24:
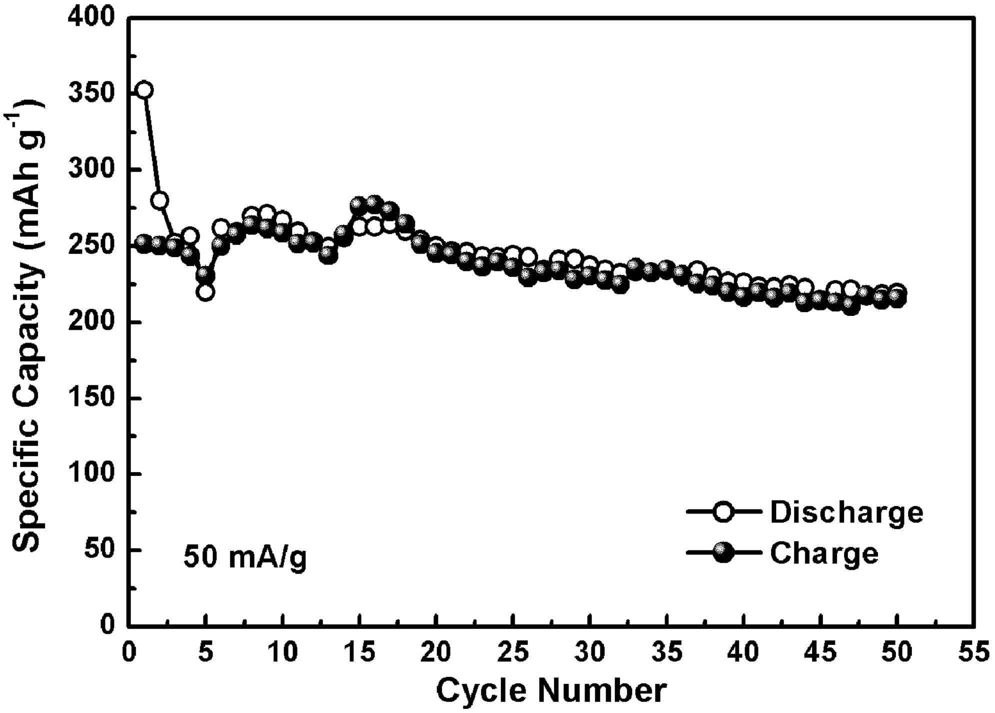
FIG. 24 shows the cyclic performance of the 1,4-DNB composite electrode of Example 2c in a Zn-ion battery at 50 mA $g^{-1}$.

FIGS. 23 and 24 show the electrochemical performance of 1,4-DNB composite cathode for Zn-ion batteries. FIG. 23 illustrates the voltage profiles of the first three charge-discharge cycles of the 1,4-DNB cathode at a mild current density of 50 mA $g^{-1}$ for Zn-ion battery. The operating voltage plateau within 0.25~ 0.5 V is observed, along with a high initial capacity of 355 mAh $g^{-1}$. Cycling at 50 mA $g^{-1}$ (FIG. 24) confirms its high stability, with a terminal capacity of 220 mAh $g^{-1}$ retained after 50 cycles.

Example 2d—1,4-Dinitrobenzene for Al-ion Batteries 1,4-DNB has also been used and evaluated as a cathode material for Al-ion batteries. The cathodes were prepared in the same way as those for Zn-ion batteries. CR2025-type coin cells were assembled with the 1,4-DNB composite cathode and an aluminum metal foil as the anode, which were separated with a glass fiber separator. The electrolyte employed contained $AlCl_3$ in an ionic liquid $EMIMAlCl_4$ at a molar ratio of 1:1.5.

Figure 25:
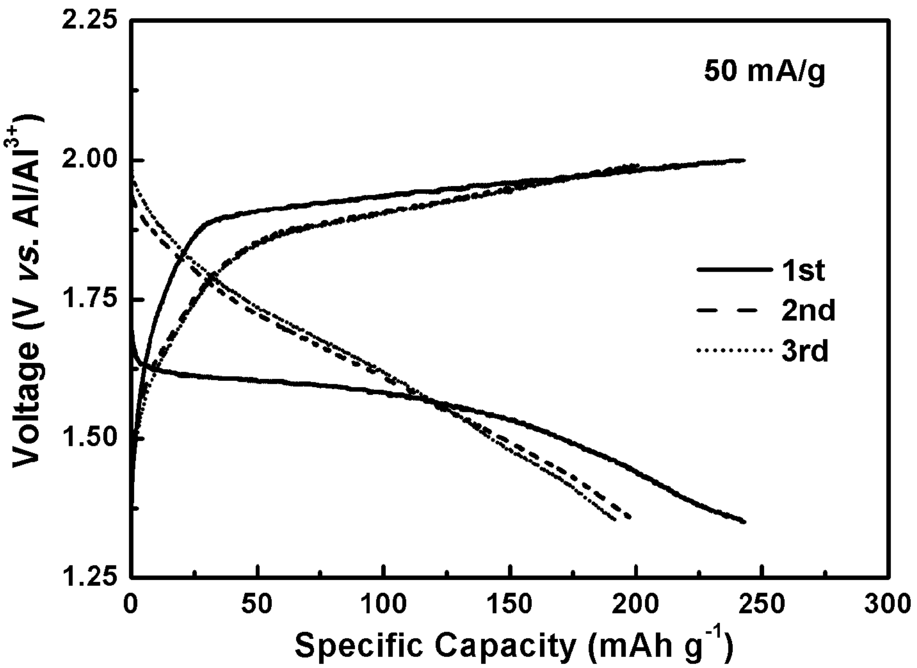
FIG. 25 shows the first three charge-discharge cycles of the 1,4-DNB composite electrode of Example 2d at 50 mA $g^{-1}$ (vs. $Al/Al^{3+}$ anode).
Figure 26:
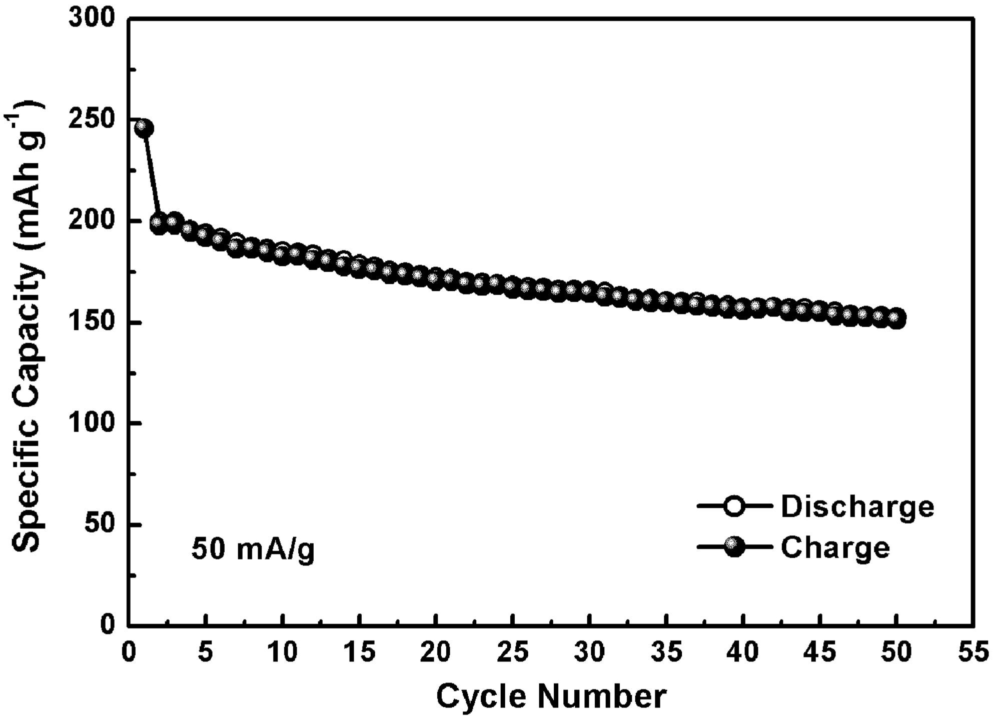
FIG. 26 shows the cyclic performance of the 1,4-DNB composite electrode of Example 2d in a Al-ion battery at 50 mA $g^{-1}$.

FIGS. 25 and 26 show the electrochemical performance of 1,4-DNB composite cathode for Al-ion batteries. FIG. 25 illustrates the voltage profiles of the first three charge-discharge cycles of the 1,4-DNB composite cathode at 50 mA $g^{-1}$ for Al-ion battery. The operating voltage plateau is higher than 1.5 V, along with a high initial capacity of 245 mAh $g^{-1}$, confirming its high capacity. Cycling at 50 mA $g^{-1}$ (shown in FIG. 26) confirms its high stability, with a terminal capacity of 155 mAh $g^{-1}$ retained after 50 cycles.

Example 2e—1,4-Dinitrobenzene for Mg-ion Batteries 1,4-DNB was further used and evaluated for its performance as the cathode material for Mg-ion batteries. The cathode was prepared in the same way as the above one for Zn-ion batteries. CR2025-type coin cells were assembled with 1,4-DNB cathode and magnesium metal foil as the anode, which were separated with a glass fiber separator. The electrolyte employed contained 0.2 M $Mg(ClO_4)_2$ in DMSO as the solvent.

Figure 27:
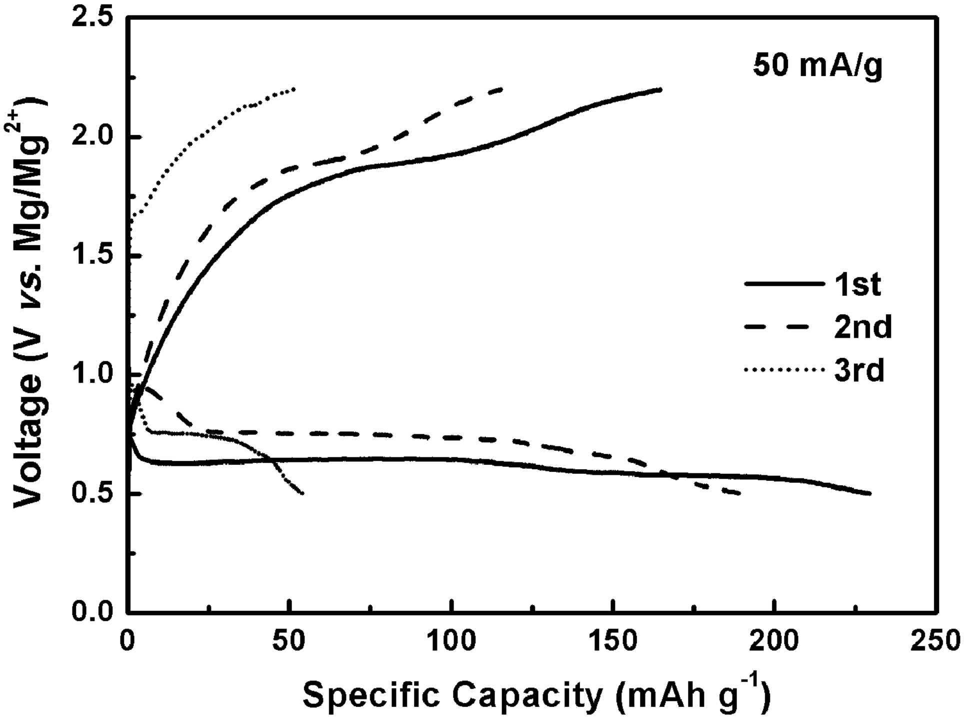
FIG. 27 shows the first three charge-discharge cycles of the 1,4-DNB composite electrode of Example 2e at 50 mA $g^{-1}$ (vs. $Mg/Mg^{2+}$ anode).

FIG. 27 shows the electrochemical performance of 1,4-DNB cathode for Mg-ion batteries. FIG. 27 illustrates the voltage profiles of the first three charge-discharge cycles of the 1,4-DNB cathode at 50 mA $g^{-1}$ for Mg-ion battery. The operating voltage plateau is around 0.75 V, along with a high initial capacity of 230 mAh $g^{-1}$.

Example 2f—1,2-Dinitrobenzene and 1,3-Dinitrobenzene for Li-ion Battery 1,2-Dinitrobenzene (1,2-DNB, 99%, Aldrich®) and 1,3-dinitrobenzene (1,3-DNB, 99%, Aldrich®) were investigated as cathode materials for Li-ion batteries. Their composites with porous conductive carbon (DNB/carbon mass ratio=40:60) were prepared as follows. Each of them was dissolved in THF, followed by the addition of the prescribed amount of the porous conducting carbon. The mixture was sonicated for 20 min and stirred with a magnetic stirrer at 400 rpm overnight at room temperature and was subsequently dried under vacuum to yield the solid mixtures. The solid mixture was then sealed in a glass tube and annealed at 180° C. for 18 h to render the composite after cooling.

1,2-DNB and 1,3-DNB composite electrodes were prepared by coating the homogeneous dispersion of the corresponding composite, Super-P® acetylene black, and binder (Nafion®) at a weight ratio of 80:10:10 in ethanol on carbon-coated Al foil (1,2-DNB or 1,3-DNB loading of 1.5~2 mg $cm^{-2}$), followed with drying at 65° C. for 5 h and then in a vacuum oven at 50° C. for 5 h. CR2025-type coin cells were prepared with the 1,2-DNB or 1,3-DNB electrode as the cathode and lithium metal foil as the anode, which were separated with two sheets of Celgard® 2500 separators. The electrolyte employed contained 1.0 M LiTFSI in a binary solvent of DOL and DME (1:1 in volume).

Figure 28:
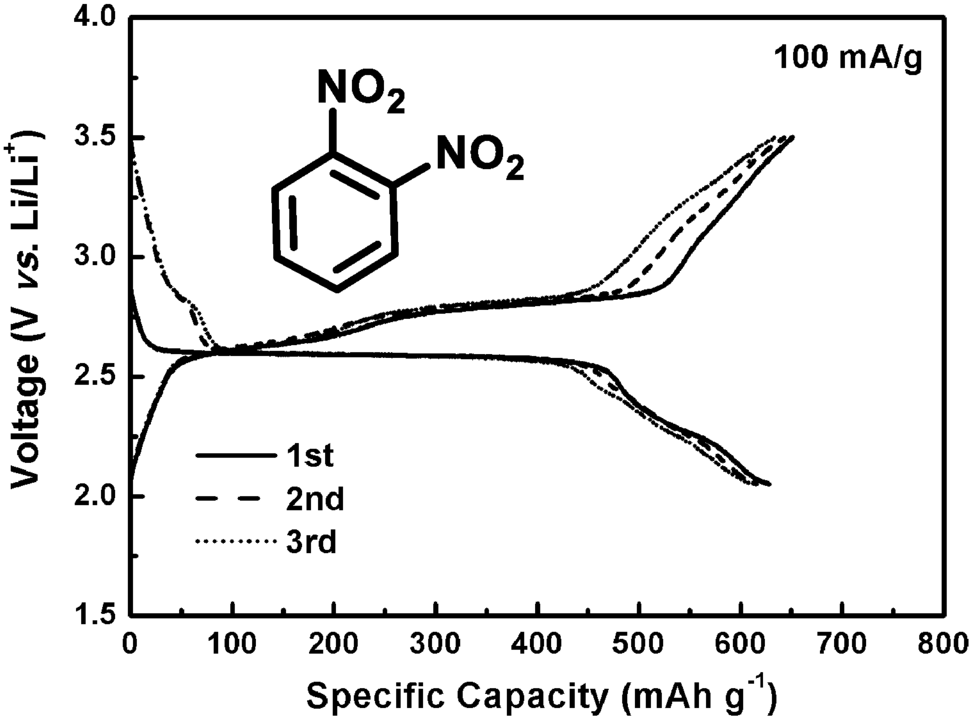
FIG. 28 shows the first three charge-discharge cycles of the 1,2-DNB composite electrode of Example 2f at 100 mA $g^{-1}$ (vs. $Li/Li^+$ anode).
Figure 29:
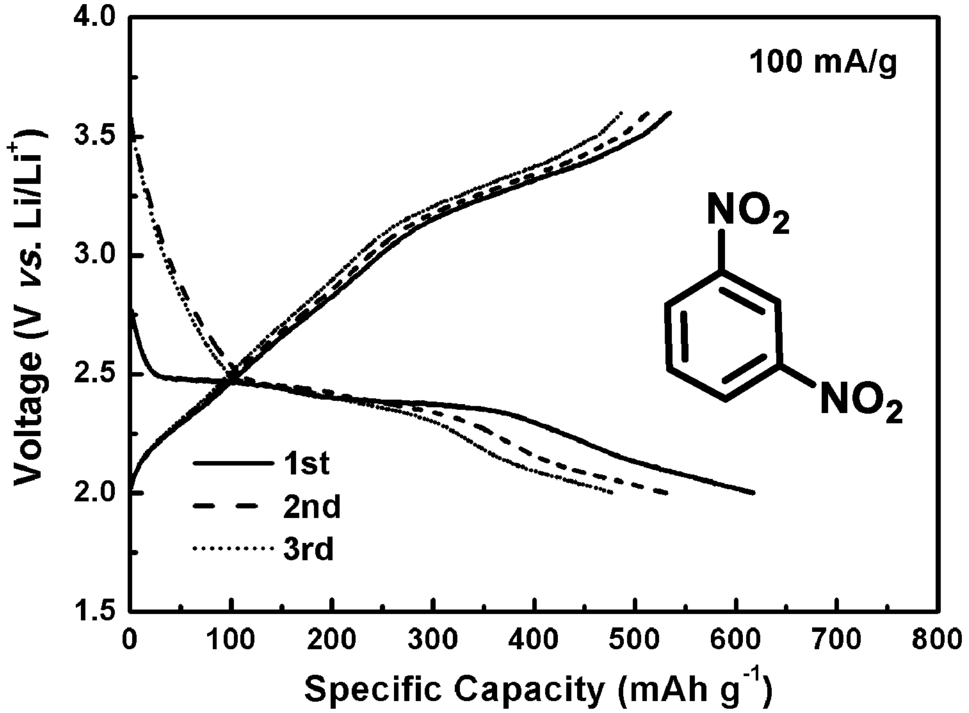
FIG. 29 shows the first three charge-discharge cycles of the 1,3-DNB composite electrode of Example 2f at 100 mA $g^{-1}$ (vs. $Li/Li^+$ anode).
Figure 30:
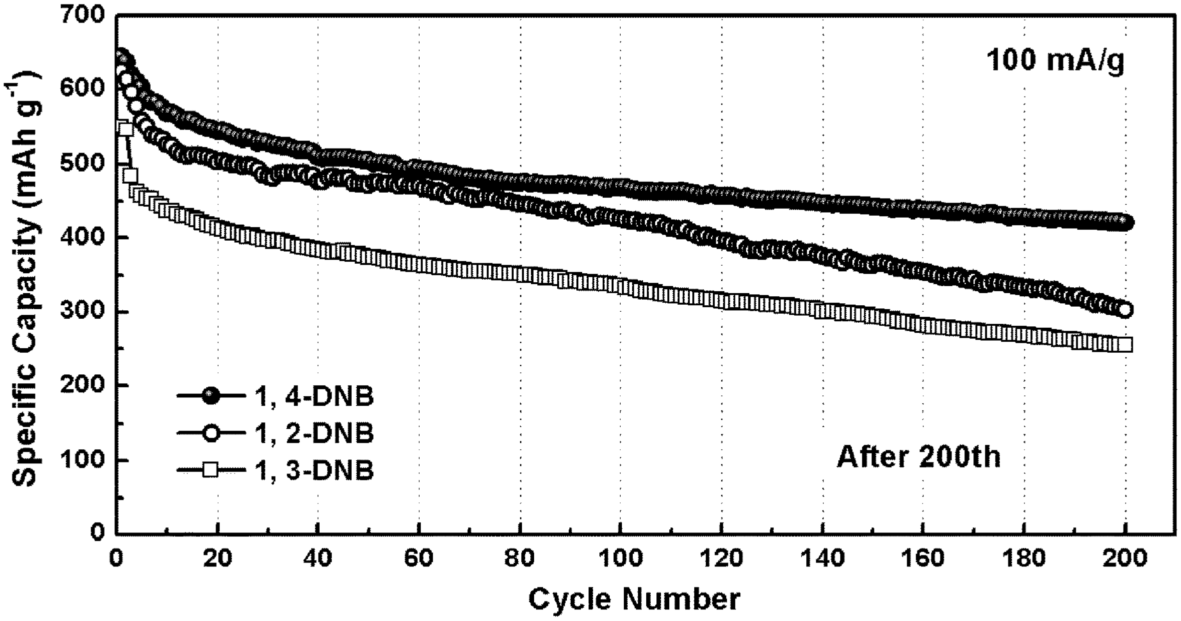
FIG. 30 shows the cyclic performance of the composite electrode of Example 2a and the 1,2-DNB and 1,3-DNB composite electrodes of Example 2f at 100 mA $g^{-1}$.
Figure 31:
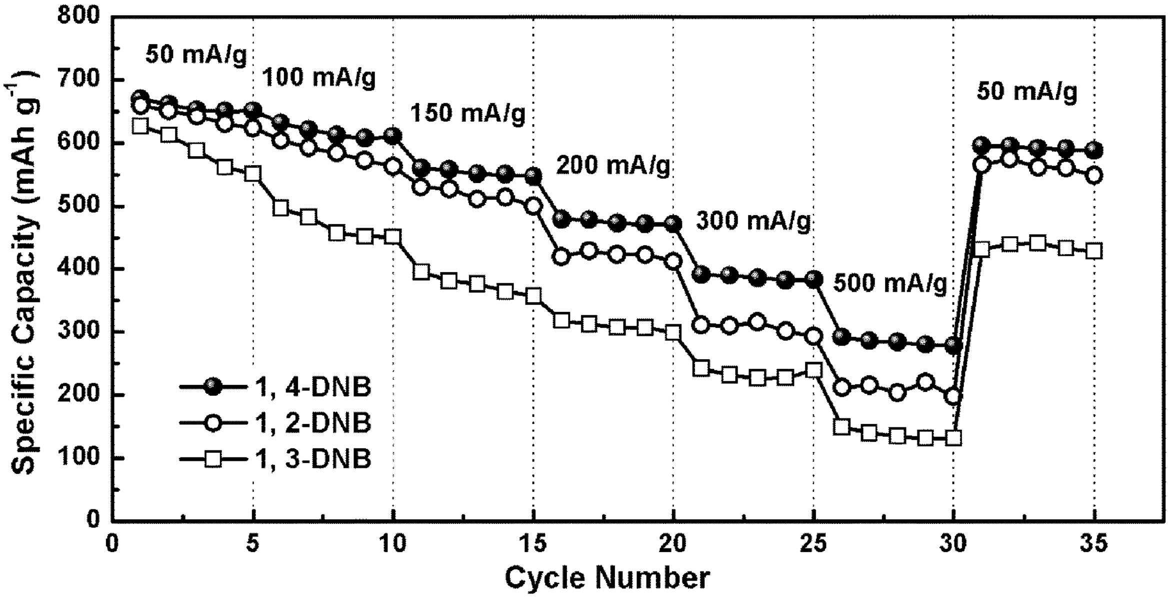
FIG. 31 shows the rate performance of the composite electrode of Example 2a and the 1,2-DNB and 1,3-DNB composite electrodes of Example 2f at various current densities (50 to 500 mA $g^{-1}$).

FIGS. 28-31 shows the electrochemical testing results of the 1,2- and 1,3-DNB composite cathodes along with comparisons with 1,4-DNB. FIGS. 28 and 29 can be compared to FIG. 4 (1,4-DNB). FIGS. 30 and 31 show the results for 1,4-DNB for comparison.

Example 2g—3,5-Dinitrobenzoic Acid for Li-ion Battery 3,5-Dinitrobenzoic acid (3,5-DNBA, 99%, Aldrich®) was investigated as a dinitrobenzene derivative with a functional substituting group for its performance as a cathode material.

The composite of 3,5-DNBA with porous conducting carbon (mass ratio=40:60) was prepared similarly as in the previous examples. Its electrodes were prepared by coating the homogeneous dispersion of the composite, Super-P® acetylene black, and binder (Nafion®) at a weight ratio of 80:10:10 in ethanol on carbon-coated Al foil with 3,5-DNBA loading of 1.5~2 mg $cm^{-2}$, followed with drying.

Its performance as cathode material for Li-ion batteries has been evaluated. CR2025-type coin cells were assembled with 3,5-DNBA composite electrode as the cathode and lithium metal foil as the anode, which were physically separated with two sheets of Celgard® 2500 separators. The electrolyte employed contained 1.0 M LiTFSI in a binary solvent of DOL and DME (1:1 in volume).

Figure 32:
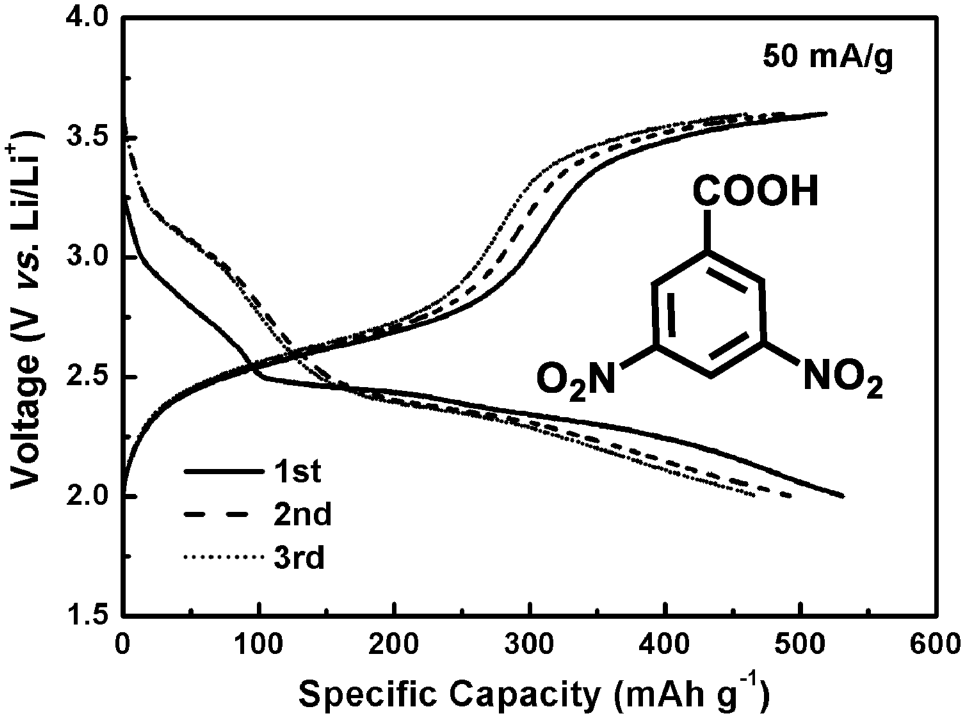
FIG. 32 shows the first three charge-discharge cycles of the 3,5-DNBA composite electrode of Example 2g at 50 mA $g^{-1}$ (vs. $Li/Li^+$ anode).
Figure 33:
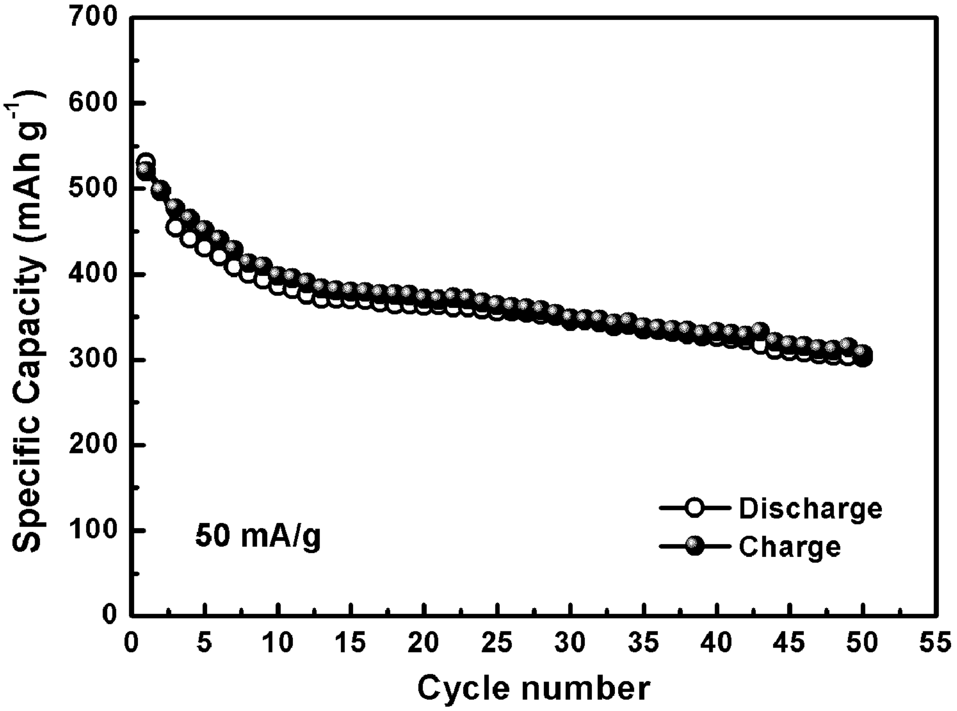
FIG. 33 shows the cyclic performance of the 3,5-DNBA composite electrode of Example 2g at 50 mA $g^{-1}$.

FIG. 32-33 shows the electrochemical performance of 3,5-DNBA composite cathodes for Li-ion batteries. FIG. 32 illustrates the voltage profiles of the first three charge-discharge cycles of the 3,5-DNBA cathode at a current density of 50 mA $g^{-1}$. Two operating voltage plateaus at 3.0 and 2.4 V, respectively, are observed, along with a high initial capacity of 540 mAh $g^{-1}$, confirming its high capacity and high working voltage. Cycling test at 50 mA $g^{-1}$ shown in FIG. 33 confirms its stability, with a terminal capacity of 310 mAh $g^{-1}$ after 50 cycles.

Example 2h—3,5-Dinitrobenzoic Acid Lithium salt for Li-ion Battery 3,5-Dinitrobenzoic acid lithium salt (3,5-DNBALi) was investigated as another dinitrobenzene derivative containing a lithium carboxylate salt substituting group for its performance as cathode material.

It was synthesized as follows. 3, 5-DNBA was dissolved in $Li_2CO_3$ aqueous solution, with a 3,5-DNBA to $Li_2CO_3$ mole ratio of 2:1. The resulting solution was dried under vacuum, followed by a final wash with acetone and centrifugation to isolate the yellow precipitate, 3,5-DNBALi.

Its composite with porous conducting carbon was prepared and used for the electrode fabrication. In specific, 3,5-DNBALi was dissolved in methanol, followed with the addition of a prescribed amount of conductive porous carbon (3,5-DNBALi/carbon mass ratio=40:60). The solution was stirred with a magnetic stirrer at 400 rpm for 12 h at room temperature and was subsequently dried under vacuum to render the composite without any further heating treatment.

Electrodes with 3,5-DNBALi as active material were prepared by coating the homogeneous dispersion of its carbon composite, Super-P® acetylene black, and binder (Nafion®) at a weight ratio of 80:10:10 in ethanol on carbon-coated Al foil as current collector at the 3, 5-DNBALi loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 34:
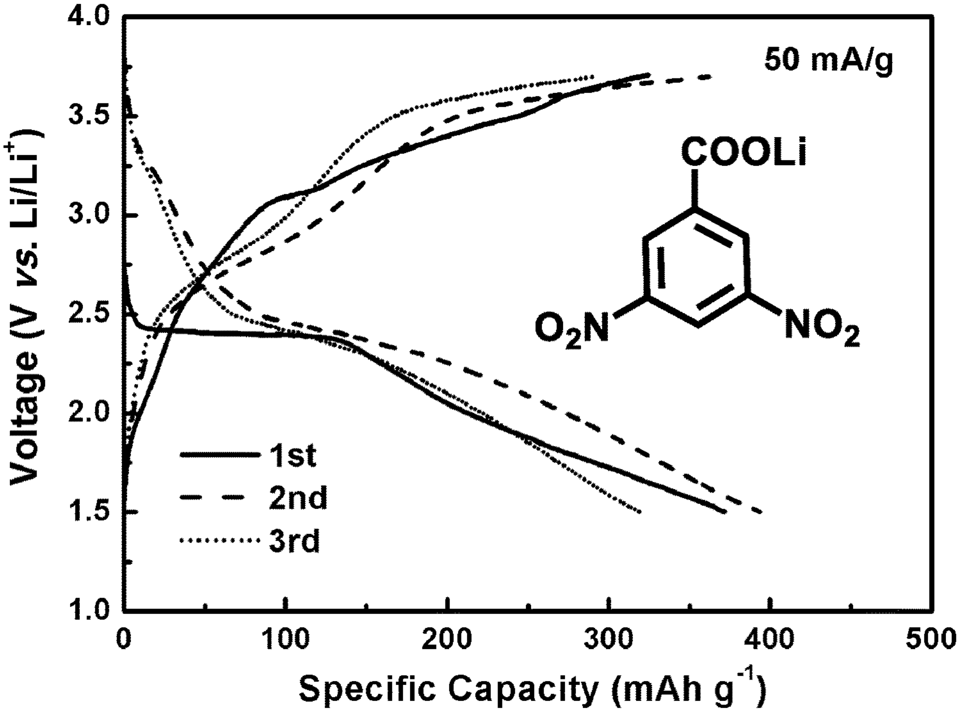
FIG. 34 shows the first three charge-discharge cycles of the 3,5-DNBALi composite electrode of Example 2h at 50 mA $g^{-1}$ (vs. $Li/Li^+$ anode).
Figure 35:
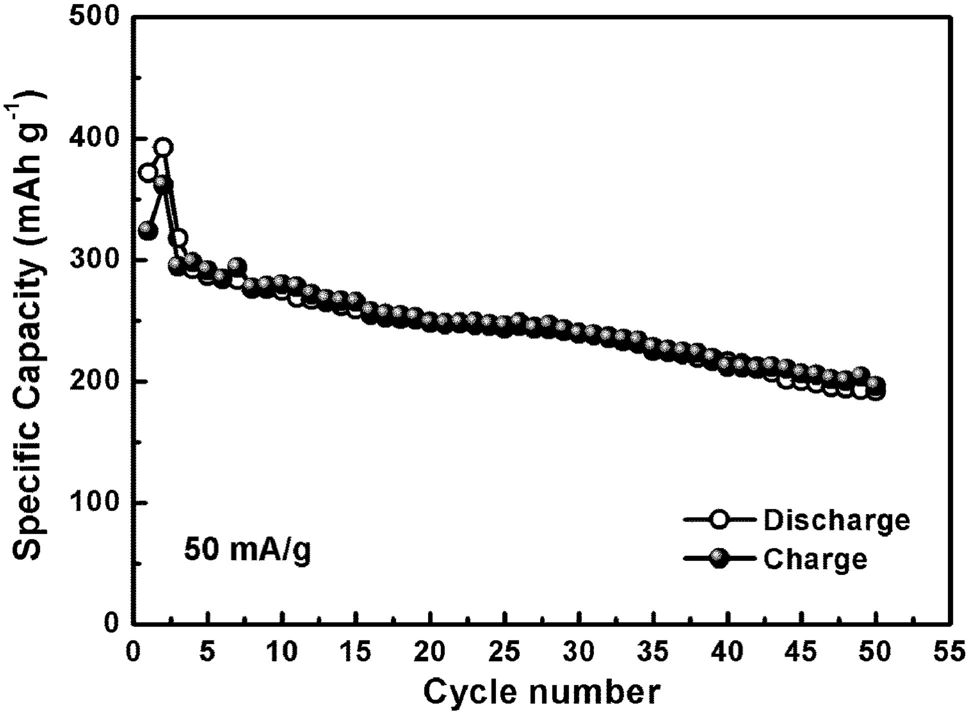
FIG. 35 shows the cyclic performance of the 3,5-DNBALi composite electrode of Example 2h at 50 mA $g^{-1}$.

FIGS. 34 and 35 show the electrochemical performance of 3, 5-DNBALi composited with porous carbon electrode for Li-ion battery. FIG. 34 illustrates the voltage profiles of the first three charge-discharge cycles of the 3,5-DNBALi cathode at a current density of 50 mA $g^{-1}$. An operating voltage plateau at 2.45 V is observed, along with a high initial capacity of 398 mAh $g^{-1}$, confirming its high capacity and high working voltage. Cycling at 50 mA $g^{-1}$ (see FIG. 35) confirms its stability, with a terminal capacity of 205 mAh $g^{-1}$ retained after 50 cycles.

Example 2i—3,5-Dinitrobenzoic Acid Sodium salt for Li-ion Battery 3,5-Dinitrobenzoic acid sodium salt (3,5-DNBANa) was investigated as another dinitrobenzene derivative containing a sodium carboxylate salt substituting group for its performance as cathode material.

It was synthesized as follows. 3,5-DNBA was dissolved in $Na_2CO_3$ aqueous solution, with a 3,5-DNBA to $Na_2CO_3$ mole ratio of 2:1. The resulting solution was dried under vacuum, followed by a final wash with acetone and centrifugation to isolate the yellow precipitate, 3,5-DNBANa.

Electrodes with pure 3,5-DNBANa as active material were prepared by coating the homogeneous dispersion of its powders, Super-P® acetylene black, and binder (Nafion®) at a weight ratio of 50:40:10 in ethanol on carbon-coated Al foil as current collector at the 3,5-DNBANa loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 36:
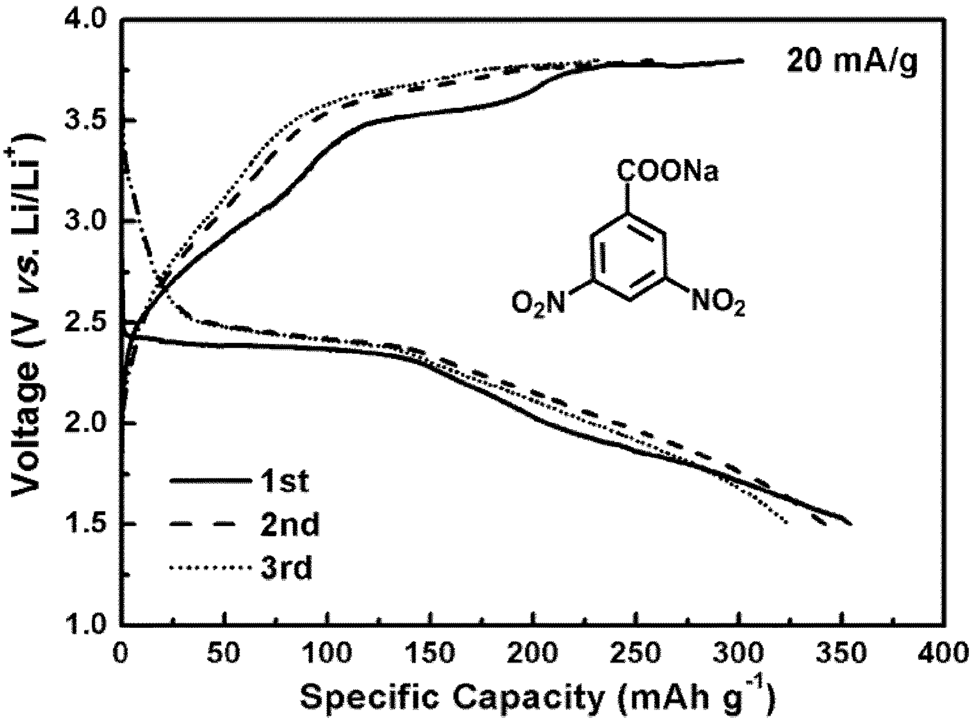
FIG. 36 shows the first three charge-discharge cycles of the 3,5-DNBANa electrode of Example 2i at 20 mA $g^{-1}$ (vs. $Li/Li^+$ anode).

FIG. 36 illustrates the voltage profiles of the first three charge-discharge cycles of a 3,5-DNBANa cathode at a current density of 50 mA $g^{-1}$. An operating voltage plateau at 2.45 V is observed, along with a high initial capacity of 354 mAh $g^{-1}$, confirming its high capacity and high working voltage.

Example 2j—3,5-Dinitrobenzoic Acid Potassium salt for Li-ion Battery 3,5-Dinitrobenzoic acid potassium salt (3,5-DNBAK) was investigated as another dinitrobenzene derivative containing a potassium carboxylate salt substituting group for its performance as cathode material.

It was synthesized as follows. 3, 5-DNBA was dissolved in $K_2CO_3$ aqueous solution, with a 3,5-DNBA to $K_2CO_3$ mole ratio of 2:1. The resulting solution was dried under vacuum, followed by a final wash with acetone and centrifugation to isolate the yellow precipitate, 3,5-DNBAK.

Electrodes with 3,5-DNBAK as active material were prepared by coating the homogeneous dispersion of its powders, Super-P® acetylene black, and binder (Nafion®) at a weight ratio of 50:40:10 in ethanol on carbon-coated Al foil as current collector at the 3, 5-DNBAK loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 37:
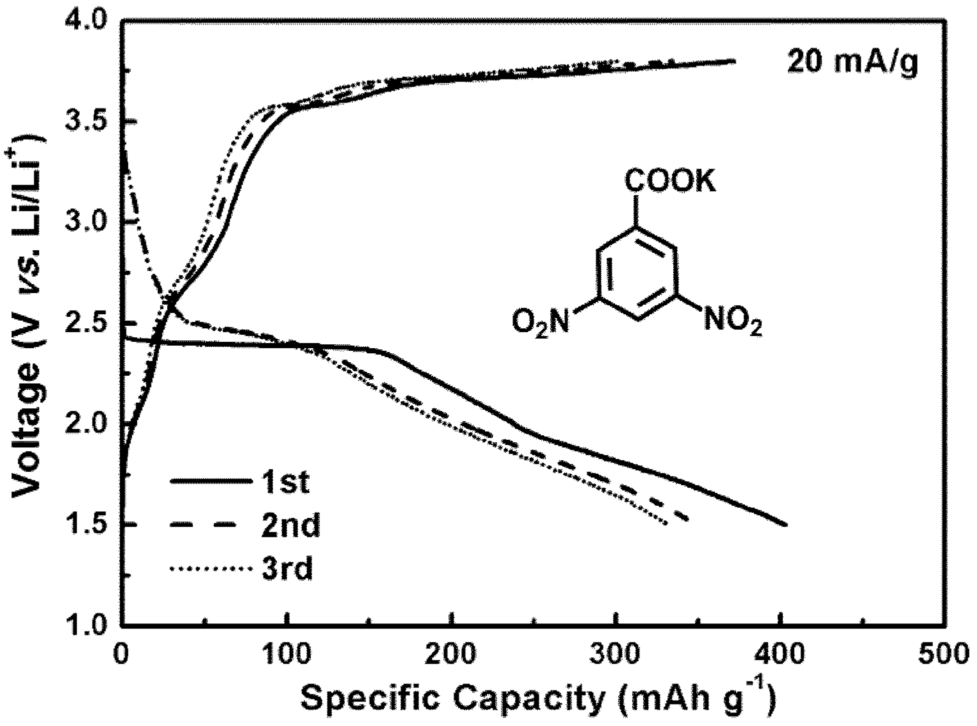
FIG. 37 shows the first three charge-discharge cycles of the 3,5-DNBAK electrode of Example 2j at 20 mA $g^{-1}$ (vs. $Li/Li^+$ anode).

FIG. 37 illustrates the voltage profiles of the first three charge-discharge cycles of a 3,5-DNBAK cathode at a current density of 50 mA $g^{-1}$. An operating voltage plateau at 2.45 V is observed, along with a high initial capacity of 403 mAh $g^{-1}$, confirming its high capacity and high working voltage.

Example 3—Representative Dinitro-Substituted Naphthalenes

Example 3a—1,5-dinitronaphthalene & Example 3b—1,8-dinitronaphthalene

Two representative dinitro-substituted naphthalenes, 1,5-dinitronaphthalene (1,5-DNN, 97%, Fisher) and 1,8-dinitronaphthalene (1,8-DNN, 85%, Fisher), have been evaluated for their performance as the cathode materials.

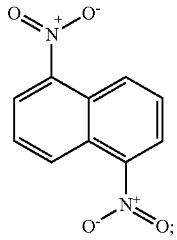

1,5-dinitronaphthalene (1,5-DNN)

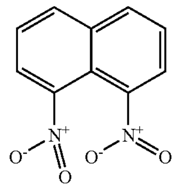

1,8-dinitronaphthalene (1,8-DNN)

Their electrodes were prepared by coating a homogeneous slurry of 1,5- or 1,8-DNN, Super-P® acetylene black, and binder (Nafion®) at a weight ratio of 60:30:10 in ethanol on a carbon-coated Al foil as the current collector with the DNN loading of 1.5~2 mg $cm^{-2}$, followed with drying. Electrochemical performances of the electrodes were tested in CR2025-type coin cells assembled with Li metal foil as the anode and 1.0 M LiTFSI in a binary solvent of DOL and DME (1:1 in volume) as the electrolyte.

Figure 38:
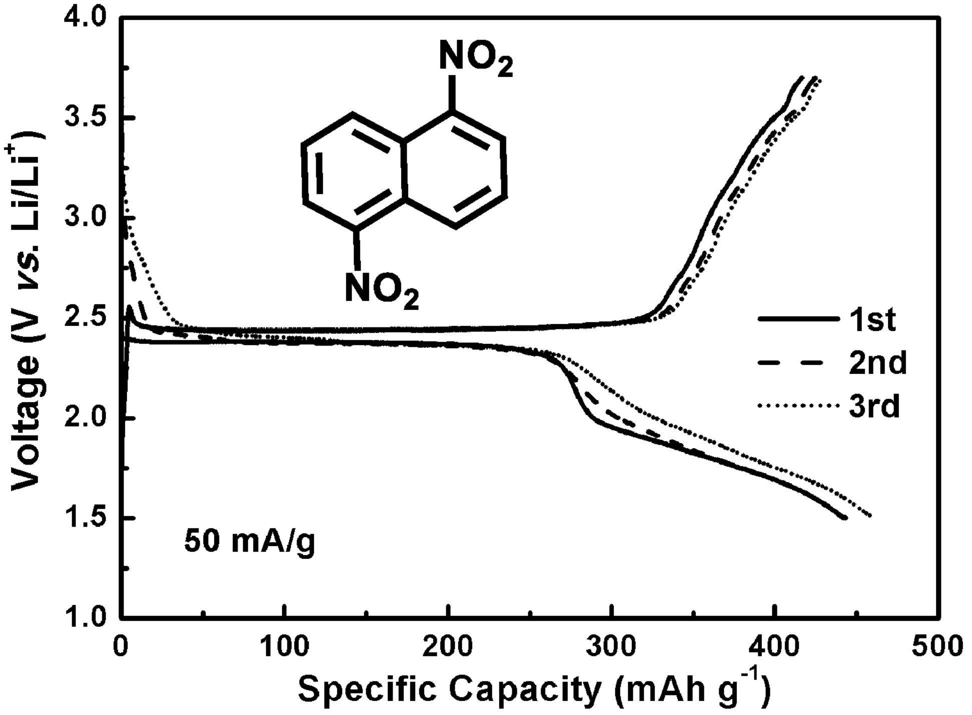
FIG. 38 shows the first three charge-discharge cycles of the 1,5-DNN composite electrode of Example 3 at 50 mA $g^{-1}$ (vs. $Li/Li^+$ anode).
Figure 39:
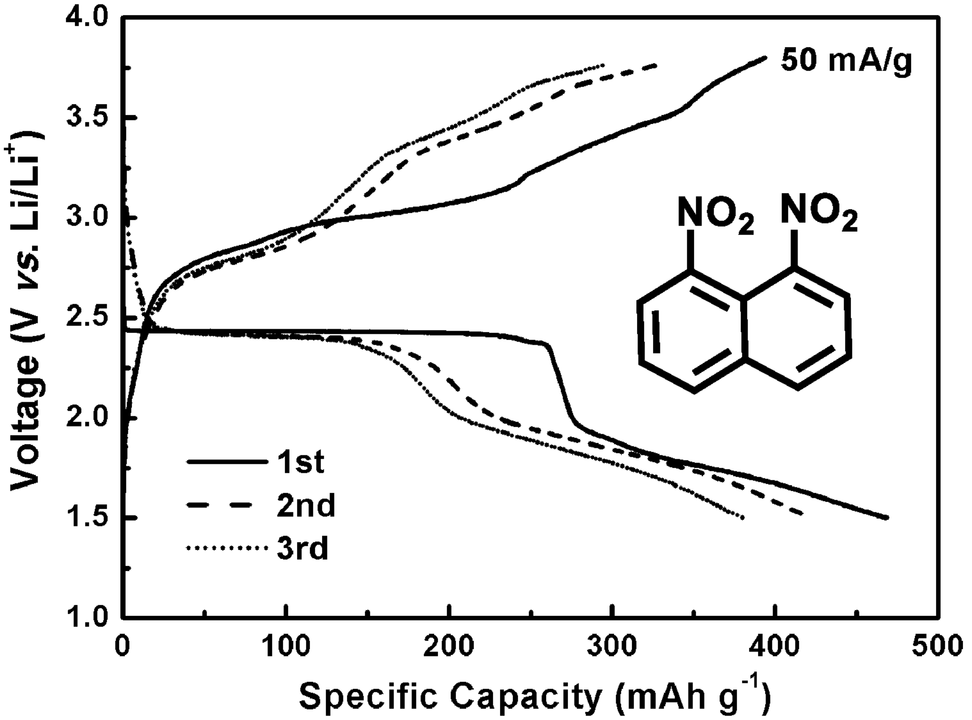
FIG. 39 shows the first three charge-discharge cycles of the 1,8-DNN composite electrode of Example 3 at 50 mA $g^{-1}$ (vs. $Li/Li^+$ anode).

FIGS. 38 and 39 shows the electrochemical performance of (a) 1,5-DNN and (b) 1,8-DNN cathodes for Li-ion batteries. These figures illustrate the voltage profiles of the first three charge-discharge cycles of 1,5-DNN and 1,8-DNN cathodes at a current density of 50 mA $g^{-1}$. Both cathodes show the two discharge voltage plateaus are at around 2.45 V and 1.8 V, respectively, along with high initial capacities of 449 and 460 mAh $g^{-1}$, confirming their high working voltages and high capacities.

Example 4—Representative Dinitro-Substituted Biphenyls 4,4'-Dinitrobiphenyl was selected as a representative molecule to demonstrate the electrochemical performances of dinitro-substituted biphenyls.

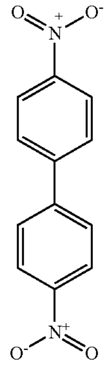

4,4'-Dinitrobiphenyl (4,4'-DNBP)

Example 4a—4,4'-Dinitrobiphenyl (4,4'-DNBP) for Li-ion battery 4,4'-Dinitrobiphenyl (4,4'-DNBP, 99%, Aldrich®) was dissolved in THF, followed with the addition of a prescribed amount of conductive porous carbon (4,4'-DNBP/C mass ratio=40:60). The dispersion was sonicated for 20 min and stirred with a magnetic stirrer at 400 rpm at room temperature, and was subsequently dried under vacuum to isolate the solid mixture. The resulting solid mixture was then sealed, under vacuum, in a glass tube and annealed at 200° C. for 18 h. After cooling to room temperature, the composite of 4,4'-DNBP with porous carbon was obtained.

A mixture of the 4,4'-DNBP composite, Super-P® acetylene black, and binder (Nafion®) at a weight ratio of 80:10:10 was mixed in ethanol to form a homogeneous slurry. Electrodes were prepared by coating the slurry on the carbon-coated Al foil with a 4,4'-DNBP loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 40:
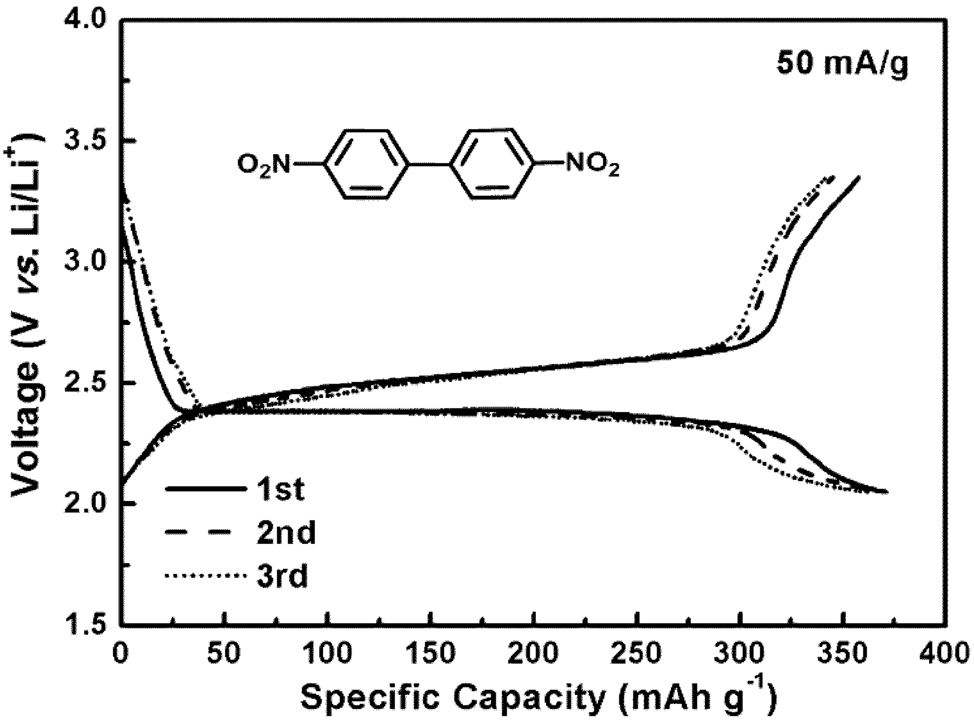
FIG. 40 shows the first three charge discharge cycles of the 4,4'-DNBP composite electrode of Example 4a at 50 mA $g^{-1}$ (vs. $Li/Li^+$ anode).
Figure 41:
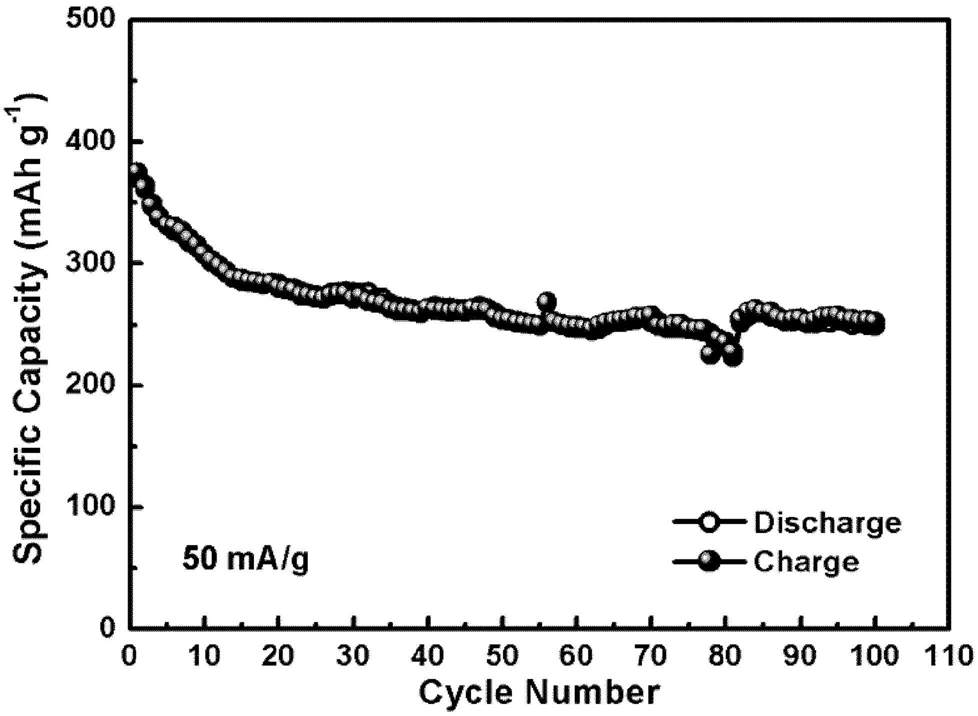
FIG. 41 shows the cyclic performance of the 4,4'-DNBP composite electrode of Example 4a at 50 mA $g^{-1}$.

FIGS. 40 and 41 show the electrochemical performance of 4,4'-DNBP composited with porous carbon electrode for Li-ion battery. FIG. 40 illustrates the voltage profiles of the first three charge-discharge cycles of a 4,4'-DNBP cathode at a current density of 50 mA $g^{-1}$. An operating voltage plateau at 2.39 V is observed, along with a high initial capacity of 370 mAh $g^{-1}$, confirming its high capacity and high working voltage. Cycling at 50 mA $g^{-1}$ (see FIG. 41) confirms its good stability, with a terminal capacity of 250 mAh $g^{-1}$ retained after 100 cycles.

Example 5—Representative Trinitro-Substituted Triphenylmethanes

Tris(4-nitrophenyl)methane was selected as a representative molecule to demonstrate the electrochemical performances of trinitro-substituted triphenylmethanes.

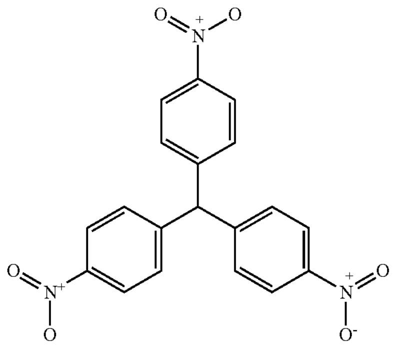

Tris(4-nitrophenyl)methane
(T4-NPM)

Example 5a—Tris(4-nitrophenyl)methane (T4-NPM) for Li-ion battery

Tris(4-nitrophenyl)methane (T4-NPM, 99%, Aldrich®) was dissolved in THF, followed with the addition of a prescribed amount of conductive porous carbon (T4-NPM/C mass ratio=40:60). The dispersion was sonicated for 20 min and stirred with a magnetic stirrer at 400 rpm at room temperature, and was subsequently dried under vacuum to isolate the solid mixture. The resulting solid mixture was then sealed, under vacuum, in a glass tube and annealed at 200° C. for 18 h. After cooling to room temperature, the composite of T4-NPM with porous carbon was obtained.

A mixture of the T4-NPM composite, Super-P® acetylene black, and binder (Nafion®) at a weight ratio of 80:10:10 was mixed in ethanol to form a homogeneous slurry. Electrodes were prepared by coating the slurry on the carbon-coated Al foil with a T4-NPM loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 42:
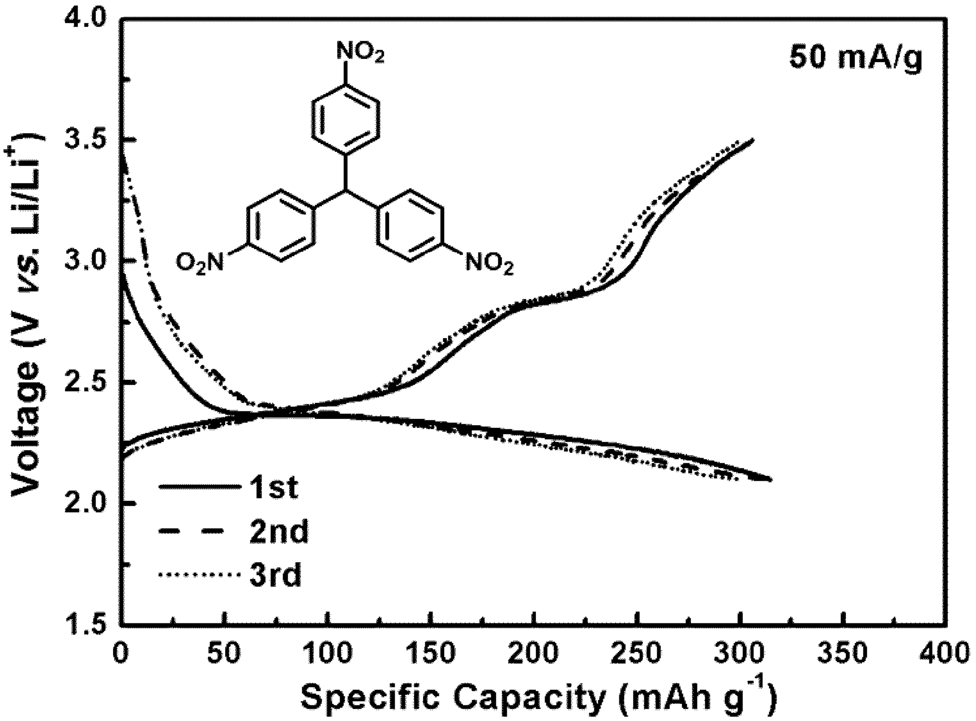
FIG. 42 shows the first three charge-discharge cycles of the T4-NPM composite electrode of Example 5a at 50 mA $g^{-1}$ (vs. $Li/Li^+$ anode).
Figure 43:
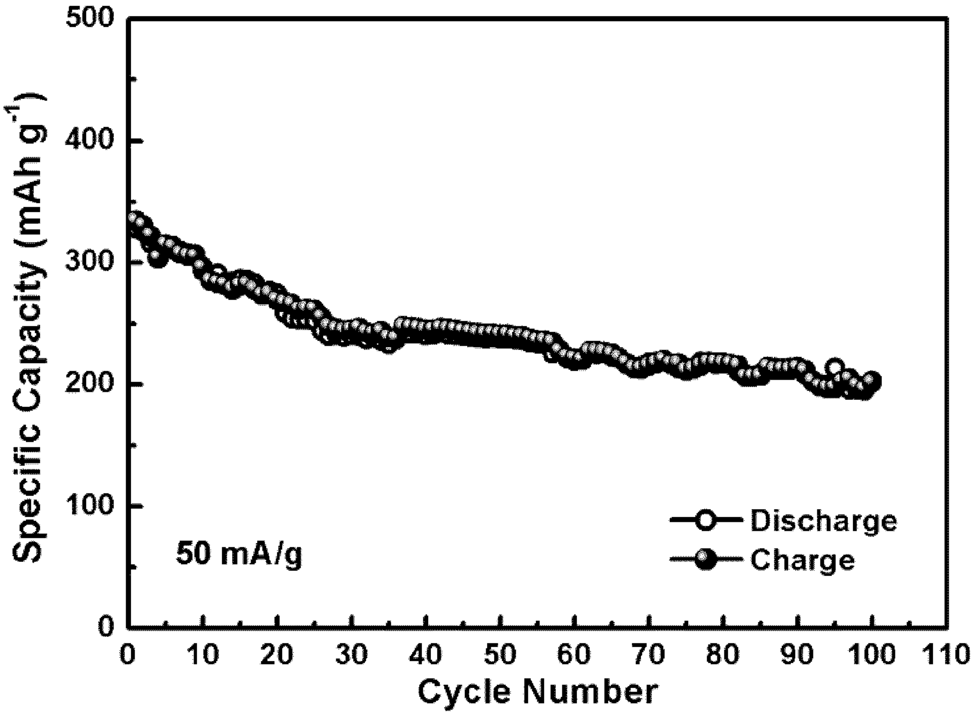
FIG. 43 shows the cyclic performance of the T4-NPM composite electrode of Example 5a at 50 mA $g^{-1}$.

FIGS. 42 and 43 show the electrochemical performances of a T4-NPM composited with porous carbon electrode for Li-ion battery. FIG. 42 illustrates the voltage profiles of the first three charge-discharge cycles of the T4-NPM cathode at a current density of 50 mA $g^{-1}$. An operating voltage plateau at 2.35 V is observed, along with a high initial capacity of 314 mAh $g^{-1}$, confirming its high capacity and high working voltage. Cycling at 50 mA $g^{-1}$ (see FIG. 43) confirms its stability, with a terminal capacity of 202 mAh $g^{-1}$ retained after 100 cycles.

Example 6—Representative Dinitro-Substituted Fluorenes 2,7-Dinitrofluorene was selected as a representative molecule to demonstrate the electrochemical performances of dinitro-substituted fluorenes.

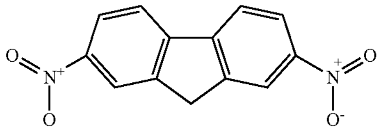

2,7-Dinitrofluorene
(2,7-DNF)

Example 6a—2,7-Dinitrofluorene (2,7-DNF) for Li-ion Battery 2,7-Dinitrofluorene (2,7-DNF, 99%, Aldrich®) was dissolved in THF, followed with the addition of a prescribed amount of conductive porous carbon (2,7-DNF/C mass ratio=40:60). The dispersion was sonicated for 20 min and stirred with a magnetic stirrer at 400 rpm at room temperature, and was subsequently dried under vacuum to isolate the solid mixture. The resulting solid mixture was then sealed, under vacuum, in a glass tube and annealed at 200° C. for 18 h. After cooling to room temperature, the composite of 2,7-DNF with porous carbon was obtained.

A mixture of the 2,7-DNF composite, Super-P® acetylene black, and binder (Nafion®) at a weight ratio of 80:10:10 was mixed in ethanol to form a homogeneous slurry. Electrodes were prepared by coating the slurry on the carbon-coated Al foil with a 2,7-DNF loading of 1.5~2 mg $cm^{-2}$, followed with drying. Electrochemical performances of the electrodes were tested on CR2025-type coin cells with Li metal foil as the anode and 1.0 M LiTFSI in a binary solvent of DOL and DME (1:1 in volume) as the electrolyte.

Figure 44:
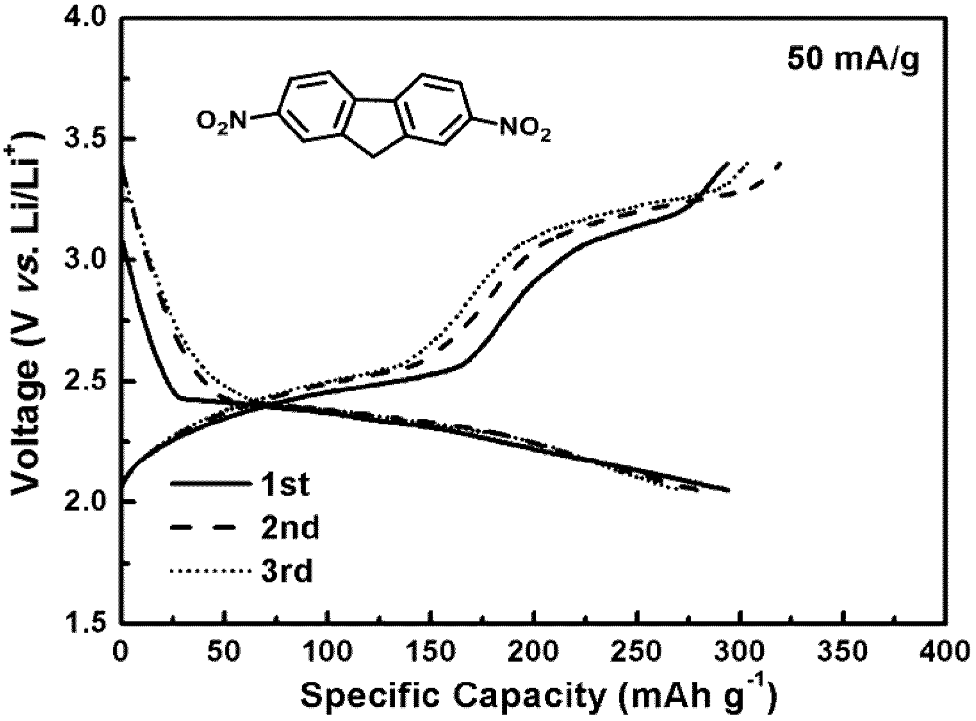
FIG. 44 shows the first three charge discharge cycles of the 2,7-DNF composite electrode of Example 6a at 50 mA $g^{-1}$ (vs. $Li/Li^+$ anode).
Figure 45:
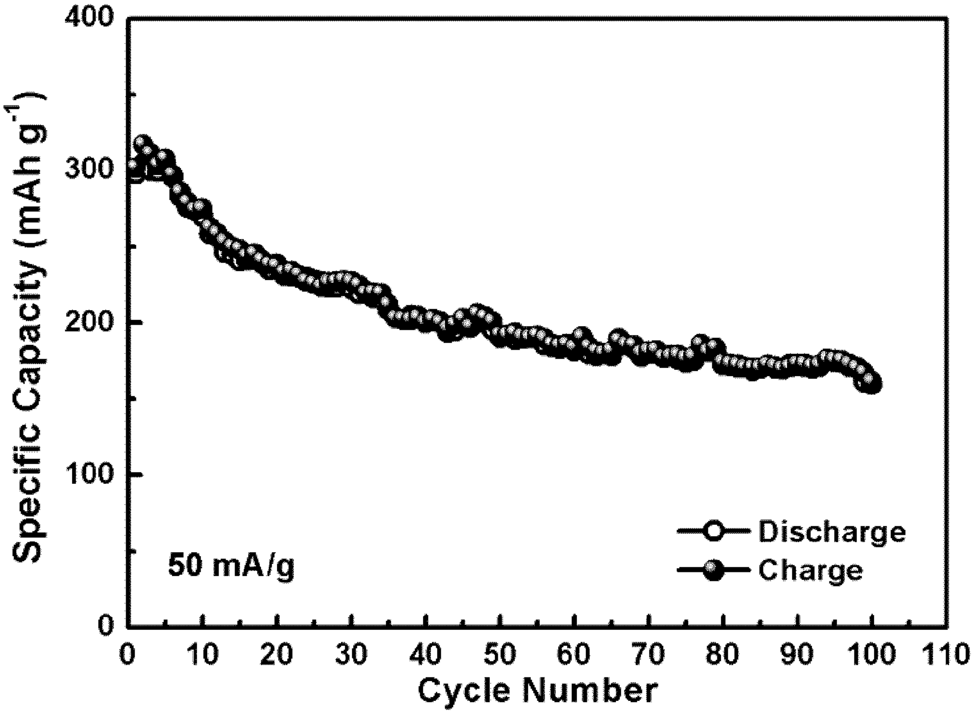
FIG. 45 shows the cyclic performance of the 2, 7-DNF composite electrode of Example 6a at 50 mA $g^{-1}$.

FIGS. 44 and 45 show the electrochemical performance of a 2,7-DNF composite electrode for Li-ion battery. FIG. 44 illustrates the voltage profiles of the first three charge-discharge cycles of the 2,7-DNF cathode at a current density of 50 mA $g^{-1}$. An operating voltage plateau at 2.36 V is observed, along with a high initial capacity of 295 mAh $g^{-1}$, confirming its high capacity and high working voltage. Cycling at 50 mA $g^{-1}$ (see FIG. 45) confirms its stability, with a terminal capacity of 160 mAh $g^{-1}$ retained after 100 cycles.

Example 7—Representative Nitro-Substituted Polymers

Poly(3-nitrostyrene) (PNS) and nitrated polystyrene (NPS) were used as representatives to demonstrate the use of polymers containing nitroaromatic groups as cathode materials. PNS and NPS have been evaluated for their performances as the cathode materials.

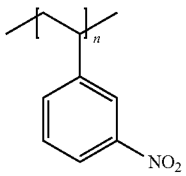

Poly(3-nitrostyrene)
(PNS)

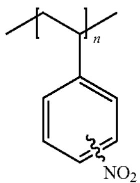

Nitrated polystyrene
(NPS)

Example 7a—Poly(3-nitrostyrene) (PNS) for Li-ion Battery

PNS was synthesized by radical polymerization of 3-nitrostyrene (3-NS, 96%, Aldrich®). The detailed procedure is as follows. A prescribed amount of 3-NS along with 5% wt. of dibenzoyl peroxide (BPO) as initiator was added into a test tube containing conductive porous carbon (3-NS/carbon mass ratio=40:60). After purge with $N_2$, the polymerization was started by heating the test tube in an oil bath set at 85° C. and lasted overnight under nitrogen protection, rendering a black composite with PNS produced inside the pores of conductive porous carbon. The composite was washed with methanol and dried under vacuum at 50° C.

PNS electrodes were produced by coating a homogeneous dispersion of the PNS composite, Super-P® acetylene black, and binder (Nafion®) at a weight ratio of 80:10:10 in ethanol on carbon-coated Al foil with the PNS loading of 1.5~2 mg $cm^{-2}$, followed with thorough drying. CR2025-type coin cells were assembled with the PNS electrode as the cathode and lithium metal foil as the anode, along with 1.0 M LiTFSI in a binary solvent of DOL and DME (1:1 in volume) as the electrolyte.

Figure 46:
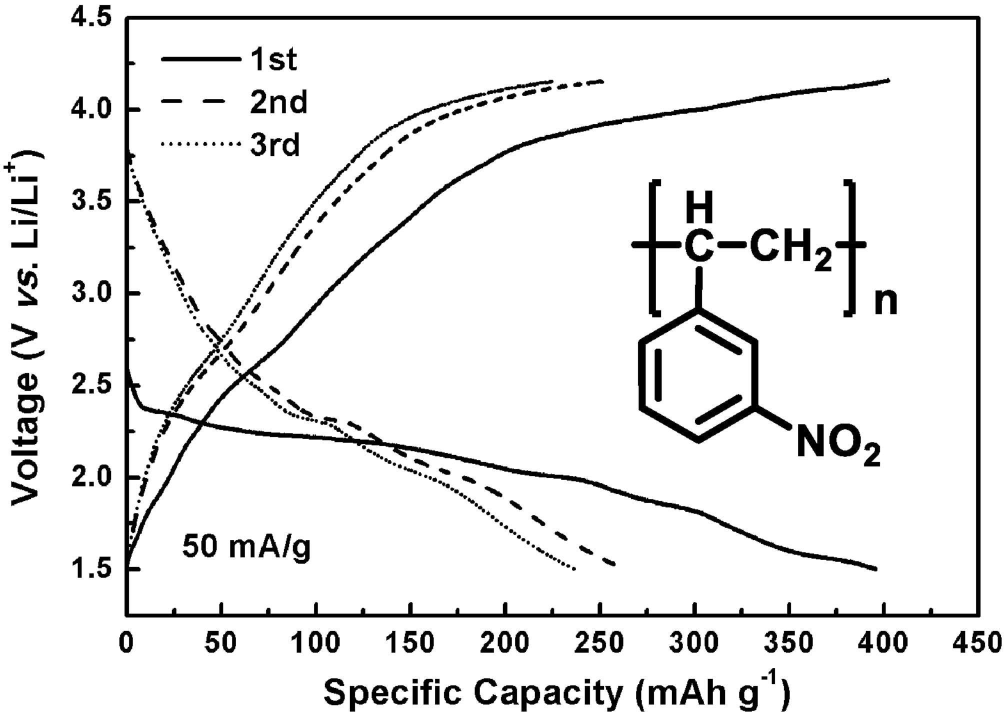
FIG. 46 shows the first three charge-discharge cycles of the poly(3-nitrostyrene) electrode of Example 7a at 50 mA $g^{-1}$ (vs. $Li/Li^+$ anode).
Figure 47:
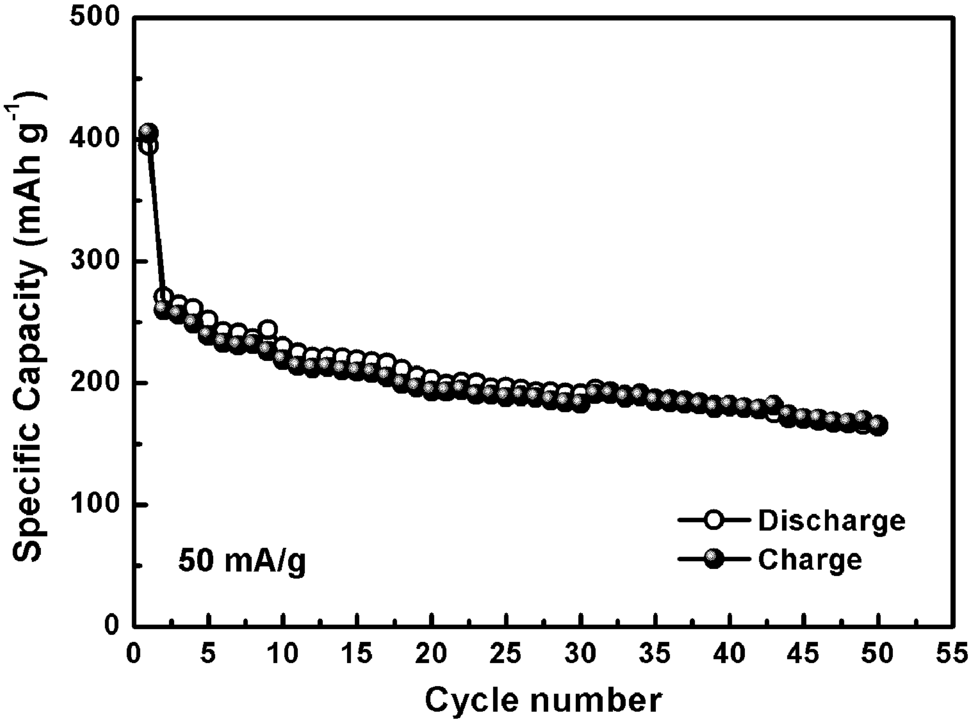
FIG. 47 shows the cyclic performance of the poly(3-nitrostyrene) electrode of Example 7a at 50 mA $g^{-1}$.

FIGS. 46 and 47 shows the electrochemical performance of a poly(3-nitrostyrene) cathode for Li-ion batteries. FIG. 46 illustrates the voltage profiles of the first three charge-discharge cycles of the poly(3-nitrostyrene) cathode at the current density of 50 mA $g^{-1}$. The operating voltage plateaus is about 2.0 V, respectively, along with a high initial capacity of 396 mAh $g^{-1}$, confirming its high capacity and high working voltage. Cycling at 50 mA $g^{-1}$ shown in FIG. 47 confirms its good stability over 50 charge-discharge cycles at 50 mA $g^{-1}$, with a terminal capacity of 165 mAh $g^{-1}$ retained after 50 cycles.

Example 7b—Nitrated Polystyrene (NPS) for Li-ion Battery

Polystyrene, from a waste polystyrene foam, was firstly dissolved in THE and stirred with multi-walled carbon nanotubes (PS:CNT=9:1 in mass) overnight followed by precipitation with methanol and drying. For nitration of the polystyrene, 200 mg of PS/CNT composite was added into a mixed acid (2 mL 70% $HNO_3$ and 5 mL 98% $H_2SO_4$) in a reaction flask. The reaction temperature was set to 60° C. and reaction time was 1 h. After washing with water until PH=7, the final composited product (NPS@CNT) was dried in the oven.

For the NPS electrode preparation, NPS@CNT was dissolved in THF, followed with the addition of a prescribed amount of conductive porous carbon (NPS@CNT/C mass ratio=1:1) to form a homogeneous slurry. Electrodes were produced by coating the homogeneous dispersion on carbon-coated Al foil with the NPS loading of 1.5~2 mg $cm^{-2}$, followed with thorough drying. CR2025-type coin cells were assembled with the NPS electrode as the cathode and lithium metal foil as the anode, along with 1.0 M LiTFSI in a binary solvent of DOL and DME (1:1 in volume) as the electrolyte.

Figure 48:
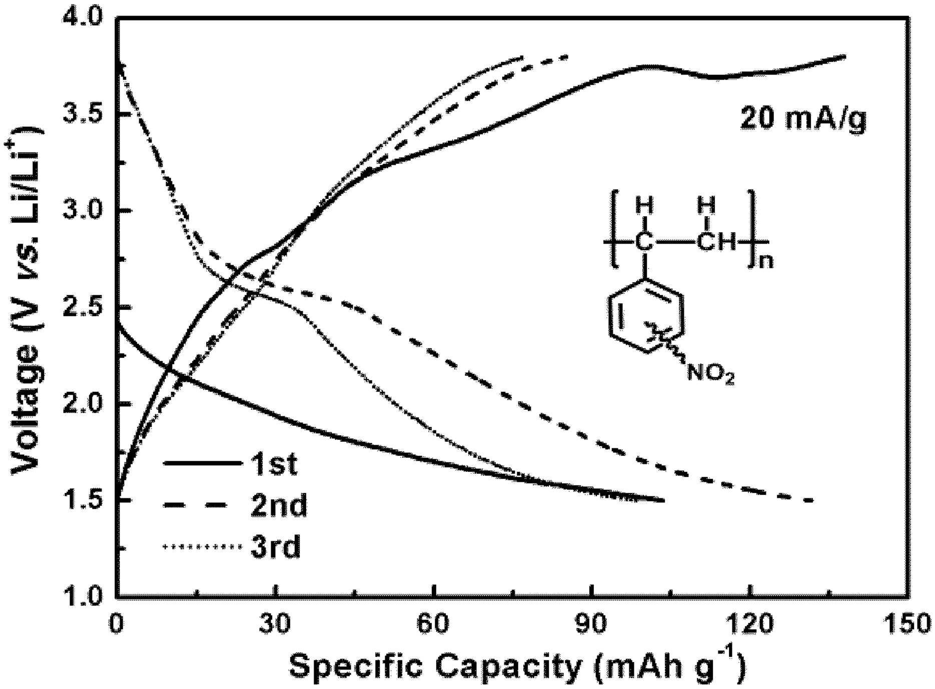
FIG. 48 shows the first three charge-discharge cycles of the nitrated polystyrene composite electrode of Example 7b at 20 mA $g^{-1}$ (vs. $Li/Li^+$ anode).
Figure 49:
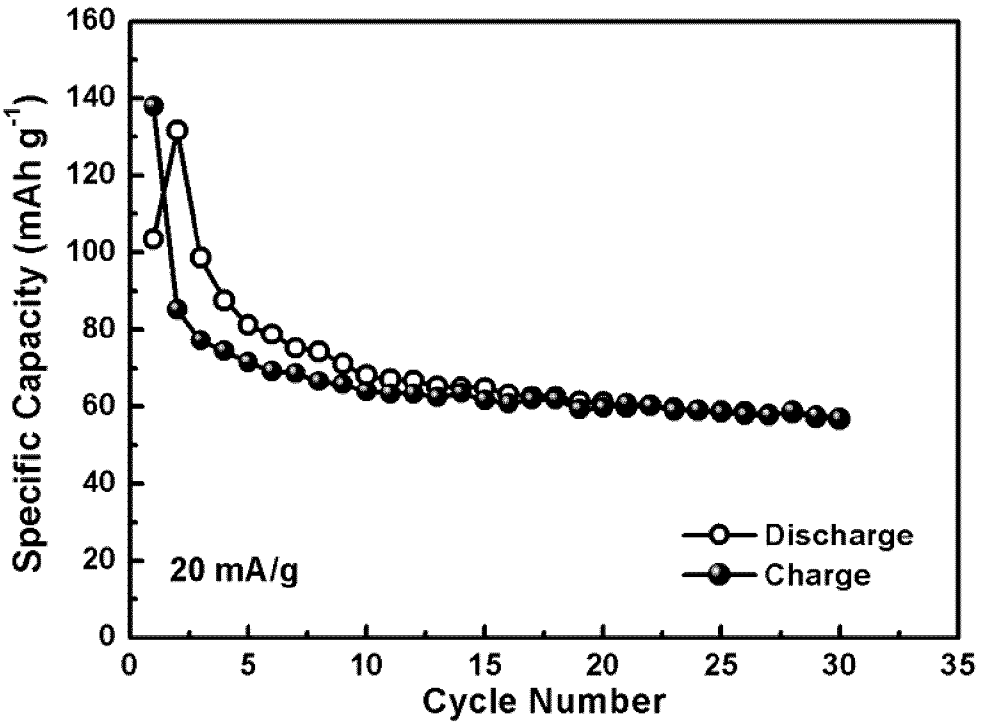
FIG. 49 shows the cyclic performance of the nitrated polystyrene composite electrode Example 7b at 20 mA $g^{-1}$.

FIGS. 48 and 49 shows the electrochemical performance of a nitrated polystyrene cathode for Li-ion batteries. FIG. 48 illustrates the voltage profiles of the first three charge-discharge cycles of the nitrated polystyrene cathode at the current density of 20 mA $g^{-1}$. The operating voltage plateaus is about 2.2 V, respectively, along with an initial capacity of 104 mAh $g^{-1}$. Cycling at 20 mA $g^{-1}$ shown in FIG. 49 confirms its good stability over 30 charge-discharge cycles at 20 mA $g^{-1}$, with a terminal capacity of 57 mAh $g^{-1}$ retained after 30 cycles.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Chinese patent application, publication no.110224140 A;
Chinese patent application, publication no.110183655 A;
Chinese patent application, publication no.109802122 A;
Chinese patent application, publication no.108767257 A;
Chinese patent application, publication no.108711624 A;
Chinese patent application, publication no.108598481 A;
Chinese patent application, publication no.106910895 A;
Chinese patent application, publication no.106654273 A;
Chinese patent application, publication no.106654200 A;
Chinese patent application, publication no.106328949 A;
Chinese patent application, publication no.106046716 A;
Chinese patent application, publication no.105206838 A;
Chinese patent application, publication no.103456961 A;
International patent application, publication no. WO 2019/068182 A1;
Japanese patent application, publication no. 2003-142100; and
Mauger et al. Recent Progress on Organic Electrodes Materials for Rechargeable Batteries and Supercapacitors, Materials 2019, 12, 1770.

The invention claimed is:

1. A secondary battery comprises a secondary battery cathode, wherein the secondary battery cathode comprises as a cathode active material a nitro-substituted aromatic compound, wherein one or more nitro groups of the nitro-substituted aromatic compound provide reversible redox-active functionality, and wherein the nitro-substituted aromatic compound is of formula (II):

(II)

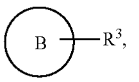

B represents an aromatic carbon allotrope, which is optionally doped with one or more heteroatoms, $R^1$ represents one or more -L-$NO_2$ substituents, wherein B is optionally further substituted by one or more $R^5$, wherein L represents a covalent bond or a linking group, and wherein each —$R^5$ independently represents $R^6$, —X, —$NH_2$, —$NR^6H$, —$NR^6_2$, —CN, —CHO, —COOH, —$COOR^6$, —$COO^-M^+$, —OH, —$OR^6$, or —$O^-M^+$ group, in which: $R^6$ represents an alkyl, alkenyl, alkynyl, aryl, or heteroaryl group, M represents a metal ion, and X represents a halogen atom; wherein -L-$R^1$ represents a number of -L-$NO_2$ substituents sufficient to functionalize the aromatic carbon allotrope.

2. A secondary battery comprises a secondary battery cathode, wherein the secondary battery cathode comprises as a cathode active material a nitro-substituted aromatic compound, wherein one or more nitro groups of the nitro-substituted aromatic compound provide reversible redox-active functionality, and wherein the nitro-substituted aromatic compound is of formula (I), (II), (III), or (IV):

(I)

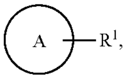

(II)

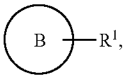

(III)

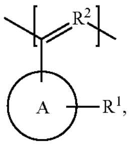

or (IV)

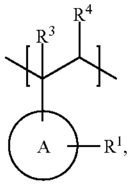

or a copolymer comprising repeat units of formula (III) and/or (IV), wherein:

A represents an arene or heteroarene,

B represents an aromatic carbon allotrope, which is optionally doped with one or more heteroatoms, $R^1$ represents one or more -L-$NO_2$ substituents, wherein in case that the nitro-substituted aromatic compound is of formula (I), $R^1$ represents at least two -L-$NO_2$ substituents;

$R^2$ represents =N—, =CH—, or =$CR^5$—, and $R^3$ and $R^4$ independently represent a hydrogen atom or $R^5$ wherein L represents a covalent bond or a linking group, and wherein each —$R^5$ independently represents $R^6$,—X, —$NH_2$, —$NR^6H$, —$NR^6_2$, —CN, —CHO, —COOH, —$COOR^6$, —$COO^-M^+$, —OH, —$OR^6$, or —$O^-M^+$ group, in which: $R^6$ represents an alkyl, alkenyl, alkynyl, aryl, or heteroaryl group, M represents a metal ion, and X represents a halogen atom; wherein A and B are substituted by one or more $R^5$ substituents.

* * * * *